(12) United States Patent
Zhu et al.

(10) Patent No.: US 9,144,229 B2
(45) Date of Patent: *Sep. 29, 2015

(54) TISSUE SPECIFIC EXPRESSION OF ANTIBODIES IN CHICKENS

(71) Applicant: Synageva BioPharma Corp., Lexington, MA (US)

(72) Inventors: Lei Zhu, Clyde Hill, WA (US); Wen Zhou, Foster, CA (US); Robert J. Etches, Oakland, CA (US)

(73) Assignee: Synageva BioPharma Corp., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/224,274

(22) Filed: Mar. 25, 2014

(65) Prior Publication Data

US 2014/0329996 A1  Nov. 6, 2014

Related U.S. Application Data

(60) Division of application No. 13/550,488, filed on Jul. 16, 2012, now Pat. No. 8,993,729, which is a continuation of application No. 11/062,325, filed on Feb. 18, 2005, now abandoned, which is a continuation-in-part of application No. 10/524,089, filed as application No. PCT/US03/25270 on Aug. 11, 2003, now abandoned, which is a continuation of application No. 10/216,098, filed on Aug. 9, 2002, now Pat. No. 7,323,618, which is a continuation-in-part of application No. 10/067,148, filed on Feb. 1, 2002, now Pat. No. 7,145,057.

(51) Int. Cl.
| | |
|---|---|
| *C12N 5/00* | (2006.01) |
| *C12N 15/00* | (2006.01) |
| *A01K 67/027* | (2006.01) |
| *C07K 16/02* | (2006.01) |
| *C12N 15/85* | (2006.01) |

(52) U.S. Cl.
CPC ......... *A01K 67/0275* (2013.01); *A01K 67/0278* (2013.01); *C07K 16/02* (2013.01); *C12N 15/8509* (2013.01); *A01K 2217/052* (2013.01); *A01K 2227/30* (2013.01); *A01K 2267/01* (2013.01); *C07K 2317/11* (2013.01); *C07K 2317/732* (2013.01); *C07K 2317/77* (2013.01)

(58) Field of Classification Search
CPC ........... A01K 2267/01; A01K 2227/30; A01K 2217/05; A01K 67/0275; A01K 2217/206; C12N 15/8509; C12N 2840/203; C12N 2830/008; C12N 2830/90; C07K 16/00; C07K 2317/23; C07K 2317/11
See application file for complete search history.

(56) References Cited

U.S. PATENT DOCUMENTS

| | | |
|---|---|---|
| 6,287,863 B1 | 9/2001 | Hodgson |
| 6,730,822 B1 | 5/2004 | Ivarie et al. |
| 7,323,618 B2 | 1/2008 | Zhu et al. |
| 8,993,729 B2 | 3/2015 | Zhu et al. |
| 2002/0108132 A1 | 8/2002 | Rapp |
| 2004/0019923 A1 | 1/2004 | Ivarie et al. |
| 2006/0053504 A1 | 3/2006 | Zhu et al. |
| 2006/0191026 A1 | 8/2006 | Zhu et al. |

FOREIGN PATENT DOCUMENTS

| | | |
|---|---|---|
| FR | 2832423 A1 | 5/2003 |
| WO | WO-99/19472 A1 | 4/1999 |
| WO | WO-00/11151 A2 | 3/2000 |
| WO | WO-00/44892 A1 | 8/2000 |
| WO | WO-00/75300 A2 | 12/2000 |
| WO | WO-02/12437 A2 | 2/2002 |
| WO | WO-02/063293 A1 | 8/2002 |
| WO | WO-02/079447 A2 | 10/2002 |
| WO | WO-03/025146 A2 | 3/2003 |
| WO | WO-03/043415 A1 | 5/2003 |
| WO | WO-03/076601 A1 | 9/2003 |
| WO | WO-2004/015123 A1 | 2/2004 |
| WO | WO-2004/019923 A1 | 3/2004 |

OTHER PUBLICATIONS

Shields et al. (2002) J. Biol. Chem., vol. 277(3), 26733-26740.*
Harvey A.J. et al. "Expression of exogenous protein in the egg white of transgenic chickens." Nature Biotechnology. Apr. 2002, vol. 19, pp. 396-399.
Ivarie, et al. "Avian transgenesis: progress towards the promise." Trends Biotechnol (2003) 21:14-19.
Ivarie, R. "Competitive bioreactor hens on the horizon." Trends Biotechnol. 24, 99-101 (2006).
Ohta, et al. "Structures of asparagine-linked oligosaccharides from hen egg-yolk antibody (IgY). Occurrence of unusual glucosylated oligo-mannose type oligosaccharides in a mature glycoprotein." Glycoconj J. Oct. 1991;8(5):400-13.
Shinkawa, T., et al., "The Absence of Fucose but not the presence of Galactose or Bisecting NAcetylglucosamine of Human IgG1 Complex-type Oligosaccharides Shows the Critical Role of Enhancing Antibody-dependent Celleular Cytotoxicity," The J. of Biological Chem, 278:5, pp. 3466-3473 (2003).

(Continued)

*Primary Examiner* — Anne Marie S Wehbe
(74) *Attorney, Agent, or Firm* — McCarter & English, LLP; Maria Laccotripe Zacharakis; Deborah L. Nagle

(57) ABSTRACT

Transgenes encoding exogenous antibodies are stably integrated into donor cells and are present in the somatic tissue of chimeric birds. The transgenes encode exogenous antibodies and are preferably expressed in the oviduct for collection in the egg. Tissue specificity is provided by selecting the content of the transgene accordingly. Birds whose genome is comprised of transgene-derived exogenous antibody-encoding DNA express exogenous antibodies having desirable chemical properties with increased therapeutic utility compared to antibodies derived from bacterial expression systems.

18 Claims, 19 Drawing Sheets

(56) References Cited

OTHER PUBLICATIONS

Yamane-Ohnuki, N., et al., "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotech & Bioeng., Wiley & Sons, Hoboken, NJ, US, 87:5, pp. 614-622 (Sep. 5, 2004).

Zhu, et al. "Production of human monoclonal antibody in eggs of chimeric chickens." Nature Biotechnology 23, 1159-1169 (2005).

Gaub et al "The chicken ovalbumin promoter is under negative control which is relieved by steroid hormones." EMBO 6(8):2313-2320, 1987.

Dierich et al "Cell-specificity of the chicken ovalbumin and conalbumin promoters." EMBO 6(8)2305-2312, 1987.

* cited by examiner

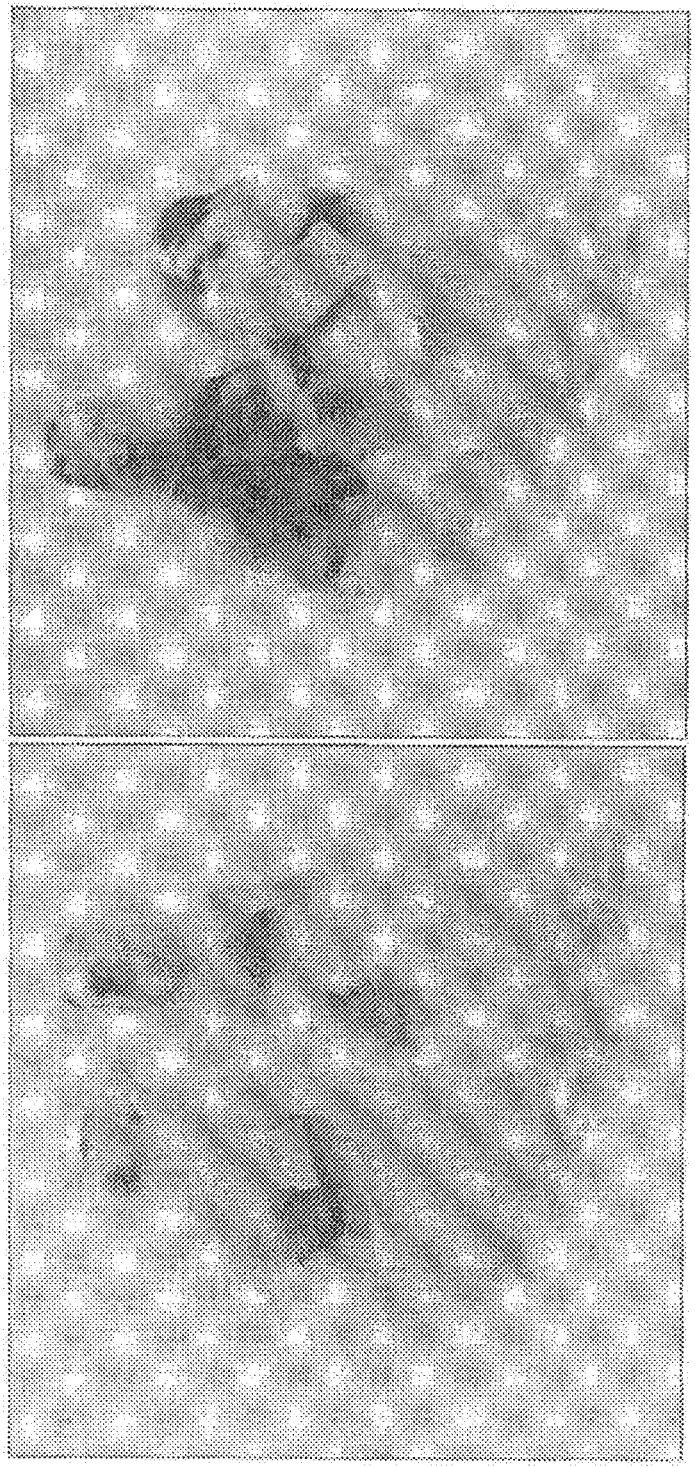

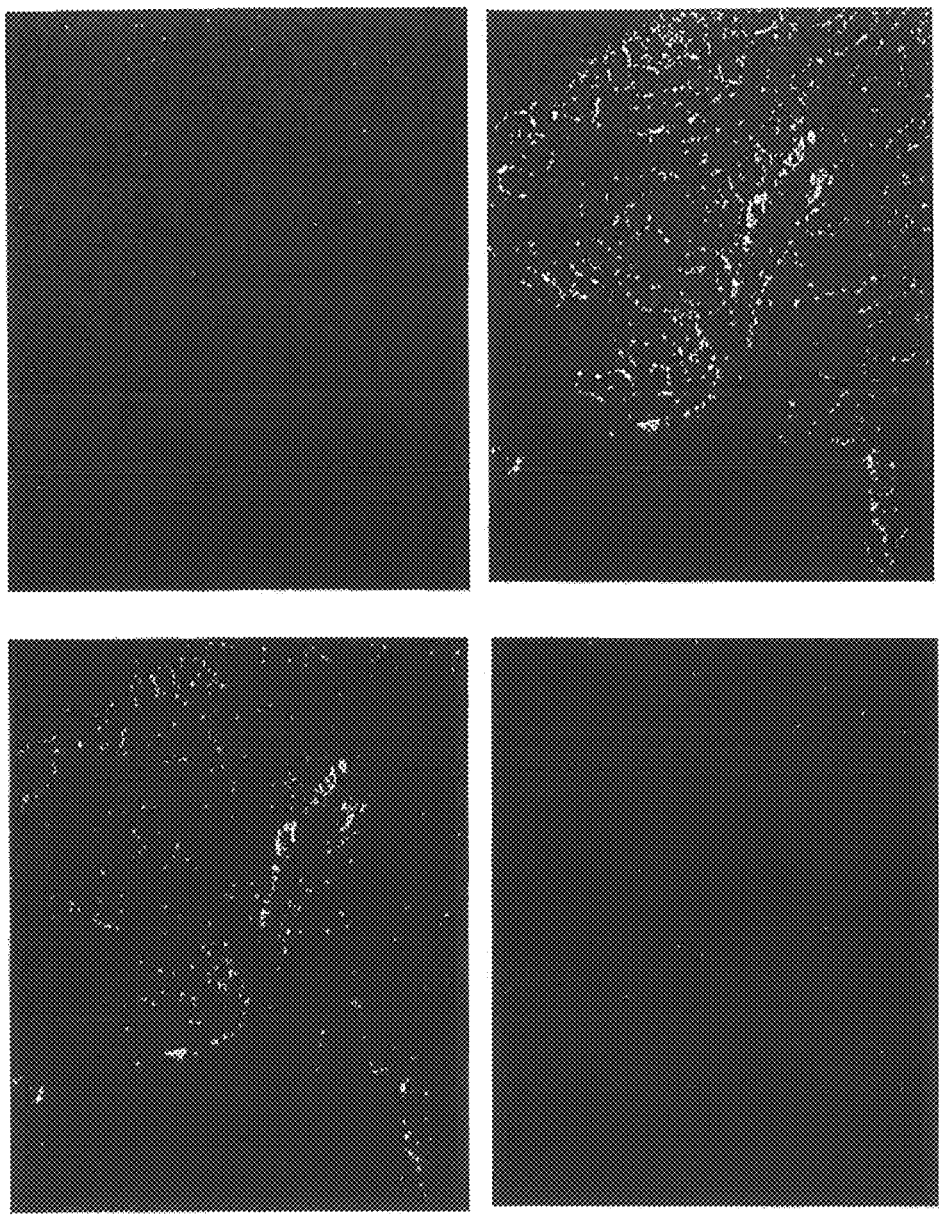
FIG. 6B  Expression of anti-dansyl MAb in tubular gland cells of 2-week female chimeras induced by estrogen

TISSUE SPECIFIC EXPRESSION OF ANTIBODIES IN CHICKENS

GOVERNMENT SUPPORT

An invention described herein may have been made with Government support under USDA SBIR 2003-33610 and NIH 2 R44 GM64261-01 and 2R44 HD 039583-02. The U.S. Government therefore has certain rights in this invention.

CROSS REFERENCE TO RELATED APPLICATIONS

This application is a divisional of U.S. application Ser. No. 13/550,488, filed Jul. 16, 2012, which is a continuation of U.S. application Ser. No. 11/062,325, filed Feb. 18, 2005, which is a continuation in part of U.S. application Ser. No. 10/524,089, filed Feb. 9, 2005, which is a U.S. National Phase Application, filed under 35 U.S.C 371 of PCT Application No. PCT/US03/25270, filed Aug. 11, 2003, which is a continuation of U.S. application Ser. No. 10/216,098, filed Aug. 9, 2002, which is a continuation in part of U.S. application Ser. No. 10/067,148, filed Feb. 1, 2002. The entire contents of all of the foregoing applications are incorporated herein by reference.

BACKGROUND OF THE INVENTION

Genetically modified animals offer the potential for tremendous advances in the sustainable production of valuable pharmaceutical products, such as antibodies. However, the production of genetically modified animals involves significant technical hurdles that have only been overcome for a few species. The ability to incorporate genetic modifications encoding proteins into the DNA of a species for a specific expression requires several distinct technologies that must be developed for each genetic modification. One approach to alter the genetic and physical characteristics of an animal is to introduce cells into recipient embryos of the animal. These cells have the ability to contribute to the tissue of an animal born from the recipient embryo and to contribute to the genome of the offspring of a resulting genetically modified animal.

Significant expenditure of time and resources has been committed to the study and development of cell lines, the manipulation of the genome of the cells, and cell culture techniques that permit such engineered cells to be maintained in culture. Although many attempts have been made, the ability to sustain the pluripotency of engineered cells in culture has been achieved for only a few species, notably mice.

If sustainable cultures were readily available and susceptible to genetic engineering while maintaining pluripotency, a broad application of new technologies would be available. Because cultured cells can contribute to the tissues of a chimeric animal, the physiological characteristics of the animal from which an embryonic stem cell was derived can be transferred to a recipient embryo by incorporating these cells into the recipient animal in an embryonic state. This offers two principal advantages: first, the phenotype of an animal from which embryonic stem cells are derived can be selectively transferred to a recipient embryo. Second, as noted above, when the cell cultures are particularly stable, the genome of the cells can be modified genetically to introduce genetic modifications into a recipient embryo in which the cells are introduced.

In certain cases, the cells can be engineered with a transgene that encodes an antibody. The transgene is a genetic construct that contains DNA that acts as the blueprint for the production of the antibody and contains sufficient coding and regulatory elements to enable the expression of the antibody in the tissue of the animal that is created from the insertion of the cells into a recipient embryo. However, the collection of a valuable antibody from the tissues of an animal typically requires that the expression be limited to certain specific tissue types that facilitate collection of the expressed protein and convey desirable chemical properties. For example, in cows, the expression of a protein in the milk enables the ready collection of the protein by simply collecting the milk of the cow and separating the exogenous protein. In chickens, the robust production of antibodies in the white of the egg also provides an attractive vehicle for the expression and collection of the antibodies. Furthermore, where the tissue specific expression is specific to the oviduct of a chicken, the expression yields antibodies having certain specific desirable chemical properties that increase the therapeutic utility of the antibodies when used in the treatment of a human patient. Thus, one particularly attractive field of research and commercial development is genetically engineered chickens that selectively express antibodies in the egg to facilitate isolation and collection of proteins with desirable chemical properties. The ability to selectively produce exogenous antibodies in specifically selected cells of an animal is particularly valuable because the absence of tissue specificity simply results in the antibody being expressed in all of the tissues of an animal. Under such circumstances, it is unlikely that a meaningful quantity of the antibody could be separated from the animal, the ubiquitous expression of an exogenous antibody is usually very damaging to the overall health and well being of the animal, and the desirable chemical properties exhibited in the chicken oviduct are not present.

If cell culture is sufficiently stable to allow a transgene to become integrated into the genome of the cell, a transgene encoding tissue specific expression of an antibody can be passed to a new chimeric or transgenic organism by several different techniques depending on the target cell and the specific construct used as the transgene. Whole genomes can be transferred by cell hybridization, intact chromosomes by microcells, subchromosomal segments by chromosome mediated gene transfer, and DNA fragments in the kilobase range by DNA mediated gene transfer (Klobutcher, L. A. and F. H. Ruddle, Annu. Rev. Biochem., 50: 533-554, 1981). Intact chromosomes may be transferred by microcell-mediated chromosome transfer (MMCT) (Fournier, R. E. and F. H. Ruddle, Proc. Natl. Acad. Sci. U.S.A., 74: 319-323, 1977). The specific design of the transgene also must consider the content of the DNA sequences encoding the antibody, the target cell line, the specific tissue in which expression is targeted, the host organism in which expression occurs, and the antibody to be expressed. The transgene designed for tissue specific expression must satisfy several parameters to enable successful integration into the genome of a cell and to insure successful expression in the selected tissue of the host organism.

As noted above, the introduction of genetic modifications to produce transgenic animals has been demonstrated in only a very few species. For mice, the separate use of homologous recombination followed by chromosome transfer to embryonic stem (ES) cells for the production of chimeric and transgenic offspring is well known. Powerful techniques of site-specific homologous recombination or gene targeting have been developed (see Thomas, K. R. and M. R. Capecchi, Cell 51: 503-512, 1987; review by Waldman, A. S., Crit. Rev. Oncol. Hematol. 12: 49-64, 1992). Insertion of cloned DNA (Jakobovits, A., Curr. Biol. 4: 761-763, 1994), and manipulation and selection of chromosome fragments by the Cre-loxP system techniques (see Smith, A. J. et al., Nat. Genet. 9: 376-385, 1995; Ramirez-Solis, R. et al., Nature 378: 720-724, 1995; U.S. Pat. Nos. 4,959,317; 6,130,364; 6,091,001; 5,985, 614) are available for the manipulation and transfer of genes into murine ES cells to produce stable genetic chimeras. Many such techniques that have proved useful in mammalian systems would be available to be applied to non-mammalian systems if the necessary long term cell cultures were available and if transgenes could be designed that yielded tissue specific expression in specific tissues that facilitate isolation and collection of the exogenous protein.

The transgenes that enable tissue specific expression are complex and the genetic manipulations that are necessary to incorporate the transgenes into a recipient cell line require extensive manipulation that can threaten the pluripotency of the cells unless the culture conditions are optimized. Thus, cell lines suitable for use in transgenesis must be both stable in culture and must maintain pluripotency when the cell is transfected with a genetic construct that is large and complex enough to contain all of the elements necessary for tissue specific expression. In the resulting animal, the transgene must be effectively expressed in specific individual tissue types in which the transgene is designed to be expressed, and should not be expressed in other tissues such that the viability of the animal or the advantageous chemistry of the resulting protein is compromised.

For the production of exogenous antibodies, avian biological systems offer many advantages including efficient farm cultivation, rapid growth, and economical production. Further, the avian egg offers an ideal biological design, both for massive synthesis of antibodies and ease of isolation and collection of product. Furthermore, as described below in the context of the present invention, advantages of the chicken-based expression system compared to vertebrate, plant, or bacterial cell systems can be obtained for large quantities of antibody product.

SUMMARY OF INVENTION

This invention includes protein expression in chickens and enabling technologies such as genetic engineering, transgenics, and the long-term culture of cells used to create chimeric and transgenic chickens. The invention also relates to antibodies produced in chickens and their unique chemistry. Specifically, these antibodies have advantageous chemical properties that enhance their therapeutic utility in certain applications. Antibodies produced in chickens have a distinct pattern of chemical modifications compared to antibodies produced in vertebrate, plant, or bacterial cell systems such that when administered to a patient with the goal of binding a toxin to target tissue, such as tumors, the target tissue is treated with increased therapeutic efficacy. In one embodiment, long term cultures of embryonic stem cells are engineered with specially designed genetic constructs to introduce genetic modification into chimeric birds, including the insertion of transgenes that yield tissue specific expression of exogenous antibodies. Transgenic birds of the invention express the transgene-derived antibody in the oviduct and the antibody is deposited in large quantities in the egg. In preferred embodiments, exogenous antibody proteins are encoded by human DNA sequences such that native human antibodies are expressed in the chicken oviduct and may be collected from the egg.

The present invention includes populations of birds exhibiting tissue specific expression of antibodies, transgene constructs that enable exogenous antibody expression, isolated compositions of antibodies produced in chickens and having specially defined chemical properties, and related methods for creation of the birds, production of the antibodies and their therapeutic use in humans. The invention uses long term cell cultures and special techniques to produce chimeric or transgenic birds derived from prolonged cell cultures, wherein the genome of the ES cells have a stably integrated transgene expressing an exogenous protein such that progeny of the cultured cells contain the stably integrated transgene. When introduced to a host avian embryo, by the procedures described below, those modified donor cells produce birds that express the transgene into specific, selected somatic tissue of the resulting animals. These birds exhibit a donor-cell derived phenotype and express the antibody in the oviduct to facilitate concentration and collection of the antibody in egg white.

This invention also includes compositions of antibodies expressed in the chicken expression system and having certain desirable chemical properties compared to vertebrate, plant, or bacterial cell systems. Specifically, the antibodies have reduced concentrations of fucose, galactose, N-acetyl neuraminic acid, N-glycolylneuraminic acid and elevated concentrations of mannose. Antibodies having some or all of these properties exhibit increased therapeutic utility when administered to a human. Specifically, these antibody compositions exhibit enhanced antibody-dependent cellular cytotoxicity (ADCC). Accordingly, the methods of the invention include enhancing the therapeutic utility, based on the ADCC effect, of compositions of antibodies by expressing them in a chicken. In practical application, the methods comprise administering the antibody composition described herein and detecting cellular cytotoxicity in the patient. The invention also includes chickens expressing exogenous antibody, having the advantageous chemistry defined herein, in the oviduct tissue such that exogenous antibody is concentrated in defined quantities in the egg white. In one preferred embodiment, the exogenous protein is a human sequence monoclonal antibody encoded by the transgene construct incorporated into the genome of a donor cell line and progeny. The human monoclonal antibody encoding polynucleotide sequence is contained within a transgene that is specifically constructed for expression in the oviduct and which contains appropriate promoters and regulatory sequences to facilitate tissue specific expression. In the embodiment of a transgenic or chimeric bird expressing exogenous proteins, the invention includes compositions specific to the animal and the protein, such as egg white albumen containing exogenous antibodies as described herein.

DESCRIPTION OF THE FIGURES

FIG. 5 are chimeras made by injecting Barred Rock ES cells into White Leghorn recipients. The pair of chimeras in the left panel exhibit minor contributions to the melanocyte lineage whereas the pair in the left panel show more extensive contributions.

FIGS. 6A and 6B are a transgene construct providing tissue specific expression in the tubular gland cells of the oviduct of a chicken and physiological evidence confirming the tissue specific expression. FIG. 6A is a diagram of a transgene containing designated Ov7.5MAbdns. FIG. 6B is a section of the magnum of a chimeric chicken containing the tissue-specific expression transgene showing the expression of monoclonal antibody selectively in tubular gland cells to the exclusion of other cell types.

DETAILED DESCRIPTION OF INVENTION

Figure 1:
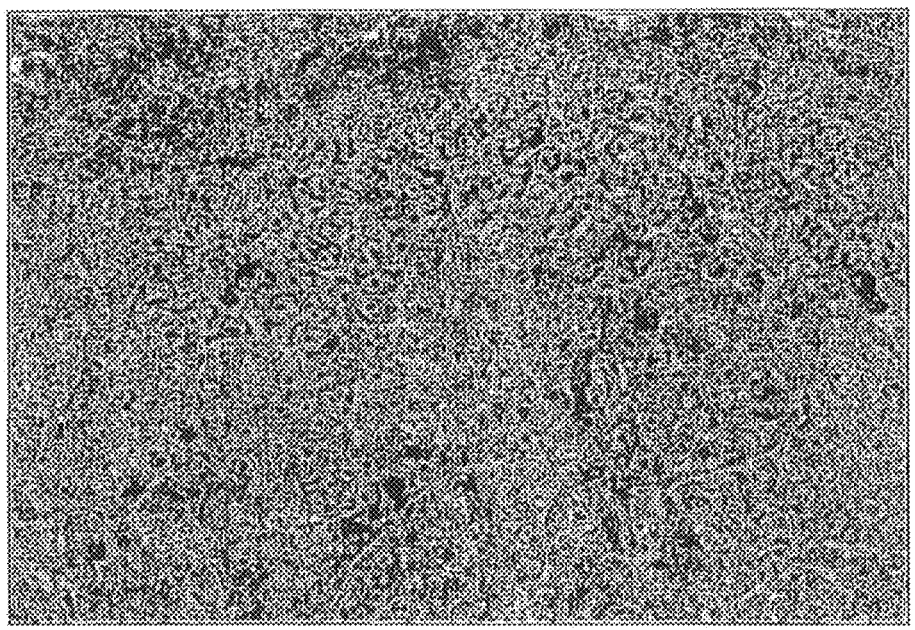
FIG. 1 shows the characteristic morphology of chicken ES cells where the cells grow in a single layer with little cytoplasm and a prominent nucleolus.

Pursuant to this invention, chicken ES cell lines are derived from stage X embryos that have a large nucleus and contain a prominent nucleolus (FIG. 1). These cells are confirmed to be chicken embryonic stem (cES) cells by morphology after long-term culturing and to yield chimeras when injected into recipient embryos. Moreover, the ES cells enable a high degree of contribution to somatic tissues as determined by extensive feather chimerism. Still further, these embryonic stem cells are demonstrated to be transfected with transgenes carrying DNA encoding an exogenous protein. The ES cells stably integrate the transgene and express the transgene to enable selection of transformed cells. These transformed cells are capable of forming chimeras wherein an exogenous protein encoded by the transgene is present in the selected tissues of the chimera. Cells derived from the chimera express the exogenous protein encoded by the transgene. In a particularly preferred embodiment, an exogenous antibody encoded by the transgene is expressed in a specific tissue or tissue type according to the antibody encoded by the transgene. Embryonic stem cell progeny are derivatives of ES cells that differentiate into non-ES cell phenotypes after introduction of the ES cells into recipient embryos and the formation of a chimera.

Broad expression of a transgene in somatic tissue is demonstrated by expression in extraembryonic and somatic tissues. Analysis of the protein content of eggs of transgenic animals demonstrates selective expression in the egg white of transgene-encoded exogenous proteins obtained from the transgenes and using the techniques of the present invention. Tissue specific expression is demonstrated by expression that is substantially confined to one organ, tissue, or cell type.

Example 1

Derivation of Chicken Embryonic Stem Cells (cES Cells)

Chicken ES cells were derived from one of two crosses: Barred Rock X Barred Rock or Barred Rock X Rhode Island Red. These breeds were selected to obtain a feather marker when testing the developmental potential of cES cells. The cES cells are injected into White Leghorn embryos, which are homozygous dominant at the dominant, white locus. Chimeric chickens resulting from injection of these ES cells display black feathers from the cES cells and white feathers from the recipient embryo.

Initial establishment of the cES cell culture was initiated according to the protocol described in U.S. Pat. No. 5,565,479. At stage X, the embryo is a small round disk, consisting of approximately 40,000-60,000 cells, situated on the surface of the yolk. To retrieve the embryo a paper ring is put on the yolk membrane, exposing the embryo in the middle. The yolk membrane is cut around the ring, which is then lifted off the yolk. The embryo, attached to the ventral side of the ring, is placed under the microscope and the area pellucida isolated from the area opaca using a fine loop.

To test for markers of pluripotency of the cells that were derived in culture, the cells were fixed and stained with SSEA-1¹ (Solter, D. and B. B. Knowles, Proc. Natl. Acad.

TABLE 1 cES cell lines derived on either STO feeder cells or a polyester insert in CES-80 medium. The cultures were initiated from both single and pooled embryos.

| Cell line | Donor embryo | Substrate used to derive cES cells | Endpoint of cell line |
|---|---|---|---|
| 009 | pooled | STO | cultured for 3 months, injected & cryopreserved |
| 029 | pooled | insert | cultured for over 3 months, injected & cryopreserved |
| 31 | pooled | STO | injected at 4 days |
| 36 | pooled | STO | injected at 13 days |
| 50 | pooled | STO | grown for over 8 months, injected & cryopreserved |
| 63b | pooled | insert | grown for 3 months and cryopreserved |
| 67I | single | insert | injected at 45 days of culture |
| 307 | pooled | STO | injected at 15 days and fixed for staining |
| 314 | pooled | STO | cultured for over 3 months, injected & cryopreserved |
| 317 | pooled | STO | injected at 12 days and fixed for staining |
| 324A | single | insert | cultured for over 6 months and injected |
| 328 | single | insert | cultured for over 6 months, injected & cryopreserved |
| 329 | single | insert | cultured for 5 months, injected & cryopreserved |
| 330 | single | insert | cultured for 3 months and cryopreserved |
| 331 | single | 24 w insert | cultured for over 3 months and terminated |
| 332 | single | 96 w STO | cultured for 3 months and cryopreserved |
| 333 | single | 12 w insert | cultured for over 3 months and terminated |
| 334 | single | 12 w insert | cultured for over 3 months and terminated |
| 335 | single | 96 w insert | cultured for over 3 months and terminated |

Embryos are dispersed mechanically into a single cell suspension and seeded on a confluent feeder layer of mitotically inactivated STO cells at a concentration of $3\times10^4$ cells/cm². The cES culture medium consists of DMEM (20% fresh medium and 80% conditioned medium) supplemented with 10% FCS, 1% pen/strep; 2 mM glutamine, 1 mM pyruvate, 1× nucleosides, 1× non-essential amino acids and 0.1 mM β-mercaptoethanol. Before use, the DMEM medium is conditioned on Buffalo Rat Liver (BRL) cells. Briefly, after BRL cells are grown to confluency, DMEM containing 5% serum is added and conditioned for three days. The medium is removed and a new batch of medium conditioned for three days and repeated. The three batches are combined and used to make the cES medium. Chicken ES cells become visible 3-7 days after seeding of the blastodermal cells. These cES cells were morphologically similar to mES cells; the cells were small with a large nucleus and a pronounced nucleolus (See FIG. 1).

The growth characteristics of cES cells are different from mES cells, which grow in tight round colonies with smooth edges and individual cells that are difficult to distinguish. Chicken ES cells grow in single layer colonies with clearly visible individual cells. Tight colonies are often the first sign of differentiation in a cES culture.

Figure 2:
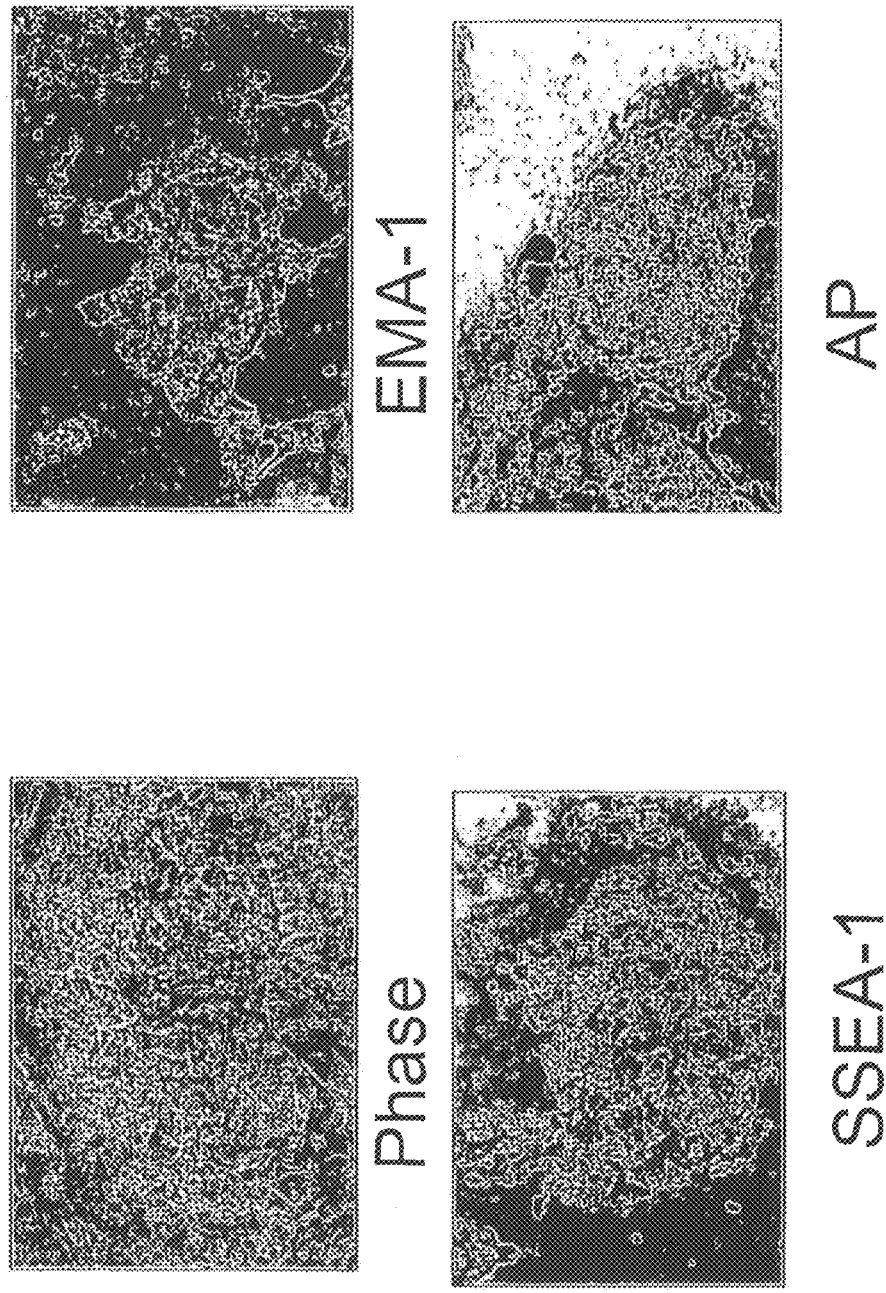
FIG. 2 shows in vitro properties of chicken ES cells, specifically the reaction with the antibodies SSEA-1 and EMA-1, and expression of alkaline phosphatase.

Sci, U.S.A. 75: 5565-5569, 1978), EMA-1, which recognize epitopes on primordial germ cells in mice and chickens (Hahnel, A. C. and E. M. Eddy, Gamete Research 15: 25-34, 1986) and alkaline phosphatase (AP) which is also expressed by pluripotential cells. The results of these tests, which are shown in FIG. 2, demonstrate that chicken ES cells express alkaline phosphatase and the antigens recognized by SSEA-1 and EMA-1.

Although cES cells are visible after using the above protocol, such cultures cannot be maintained longer than a few weeks. Several modifications in culture conditions were initiated, as discussed below, which led to the derivation of 19 cell lines (Table 1) of which 14 were tested for their developmental potential by injection into recipient embryos. Eleven of the 14 cell lines contributed to recipient embryos as determined by feather pigmentation (See Table 2 below). This protocol yields sustained cultures of pluripotent cells expressing an embryonic stem cell phenotype. At any point, the cells can be cryopreserved and when injected into compromised recipient embryos have the potential to substantially contribute to somatic tissues (See Examples 3 and 5 below).

TABLE 2

Passage number and time in culture of embryonic stem cell lines derived from single or pooled embryos. Frequency and extent of somatic chimerism after injection of these cES cells into stage X recipients.

| Cell line | Donor embryo | Passage number | time in culture (days) | # of embryos injected | # chimeras | # analyzed | % chimeras | Extent of chimerism[1] (%) |
|---|---|---|---|---|---|---|---|---|
| 31 | pooled | 0 | 4 | 15 | 2 | 7 | 28.5 | 1-5 |
| 317 | pooled | 4 | 12 | 29 | 2 | 10 | 20 | 25-65 |
| 36 | Pooled | 1 | 13 | 24 | 1 | 5 | 20 | 15 |
| 307 | pooled | 4 | 15 | 21 | 1 | 6 | 17 | 5 |
| 330 | single | 6 | 33 | 11 | 3 | 8 | 25 | 5-50 |
| 63b | pooled | 11 | 72 | 36 | 4 | 21 | 19 | 1-10 |

TABLE 2-continued

Passage number and time in culture of embryonic stem cell lines derived from single or pooled embryos. Frequency and extent of somatic chimerism after injection of these cES cells into stage X recipients.

| Cell line | Donor embryo | Passage number | time in culture (days) | # of embryos injected | # chimeras | # analyzed | % chimeras | Extent of chimerism[1] (%) |
|---|---|---|---|---|---|---|---|---|
| 67I | single | 3 | 45 | 28 | 0 | 15 | 0 | — |
| 324A | single | 10 | 65 | 25 | 0 | 15 | 0 | — |
| 009 | pooled | 20 | 61 | 27 | 0 | 9 | 0 | — |
| 329 | single | 3 | 15 | 31 | 8 | 17 | 47 | 3-75 |
| 329 | | 6 | 25 | 30 | 9 | 19 | 47 | 3-95 |
| 329 | | 6 | 28 | 26 | 1 | 12 | 8 | 23 |
| 329 | | 11 | 49 | 10 | 1 | 4 | 25 | 60 |
| 029 | pooled | 4 | 33 | 40 | 9 | 27 | 33 | 5-80 |
| 029 | | 9 | 37 | 40 | 4 | 15 | 27 | 4-15 |
| 328 | Single | 6 | 56 | 19 | 4 | 11 | 36 | 10-80 |
| 328 | | 12 | 98 | 33 | 7 | 22 | 32 | 5-50 |
| 314 | Pooled | 17 | 52 | 30 | 2 | 5 | 40 | 5-65 |
| 314 | | 15-17 | 53 | 29 | 1 | 4 | 25 | 30 |
| 314 | | 17 | 55 | 37 | 3 | 15 | 30 | 3-80 |
| 314 | | 16 | 65 | 27 | 2 | 11 | 18 | 5-40 |
| 314 | | 14 | 61 | 25 | 0 | 13 | 0 | — |
| 314 | | 16 | 65 | 32 | 3 | 14 | 21 | 10-60 |
| 314 | | 20 | 61 | 30 | 4 | 5 | 80 | 4-50 |
| 314 | | 21 | 67 | 30 | 2 | 11 | 18 | 5-15 |
| 314 | | 21 | 71 | 8 | 0 | 2 | 0 | — |
| 50 | pooled | 7 | 53 | 35 | 7 | 23 | 30 | 4-65 |
| 50 | | 14 | 106 | 36 | 3 | 21 | 14 | 10-30 |

[1]Extent of chimerism was determined by the proportion of black feathers.

As with the mouse, avian embryonic stem cells are derived on a variety of feeder layers including STO, STO-snl and others that are readily available. Leukemia Inhibitory Factor (LIF) produced by these feeders, and the addition of fetal bovine serum contributes to the maintenance of ES cells in an undifferentiated state. In a preferred embodiment of this invention, chicken ES cell cultures are initiated on a STO feeder layer. STO cells are grown to confluency, treated with 10 µg/ml mitomycin for 3-4 hours, washed, trypsinized and seeded on gelatin coated dishes at $4 \times 10^4$ cells/cm². cES cells appear to grow more rapidly when the feeder of STO cells are sparser. Reducing the STO feeder cell concentration to between $10^3$ and $10^5$, and preferably below $10^4$ cells/cm², facilitates the derivation and propagation of cES cells. However, when chicken embryonic fibroblasts and mouse primary fibroblasts are used as feeders, no cES cells were derived. Also, when previously established cES cells were plated on these feeders, all of them differentiated within 1 week.

Growing cES cells on synthetic inserts, such as polymer membranes (Costar, Transwell type) in the absence of feeders avoids contamination of the recipient embryo with feeder cells when the ES cells are injected. As Table 3 and 4 show, culturing on inserts, instead of STO feeders, facilitates the derivation of cES cells, and inserts can be used for initial derivation. However, after initially growing rapidly on inserts, the mitotic activity of the ES cells declines after 4-6 weeks of culture. To extend the culture the cells have to be transferred to a feeder of STO cells.

TABLE 3

Establishment of cES cells from single embryos on either inserts or a feeder of STO cells ($10^4$ cells/cm²).

| Substrate | # of cultures started | # of cell lines obtained |
|---|---|---|
| STO feeder | 56 | 3 (5%) |
| insert | 45 | 7 (16%) |

TABLE 4

Establishment of cES cells from pooled embryos on either a STO feeder or a synthetic insert.

| Substrate | # of cultures started | # of cell lines obtained |
|---|---|---|
| STO feeder | 73 | 7 (9.5%) |
| insert | 17 | 2 (12%) |

The data in Tables 3 and 4 show that chicken embryonic feeder cells and mouse primary fetal fibroblasts do not support the derivation or the culture of cES cells. A feeder of STO cells supports derivation and growth but only when present in a limited concentration of between $10^3$ and $10^5$ STO cells but preferably in the present embodiment at a concentration of less than or appropriately $10^4$ cells/cm². A dense STO feeder layer impairs the growth of cES cells; while the specified concentration of STO cells provides factor(s) necessary for ES cell proliferation. When the cells are sustained over an extended culture period and continue to express an embryonic stem cell phenotype, and differentiate into non-embryonic stem cell phenotypes in vivo, these cells are referred to as "ES cell progeny."

The cES cell culture medium consists of 80% conditioned medium and preferably contains certain BRL conditioned medium with factors necessary for the derivation and growth of cES cells. At a concentration of 50%, growth of the cES cells is not as reliable as in 80% conditioned medium. When the percentage of conditioned medium is reduced to less than 50%, the growth of the cES cells is affected, as evidenced by an increase in differentiated cells and, at a concentration of 30% or less, the cES cells differentiate within 1 week. This conditioned medium found necessary for the derivation and maintenance of cES cells does not maintain mES but causes their differentiation.

Fetal bovine serum is a preferred component of the ES cell medium according to the present invention and contains factors that keep cES cells in an undifferentiated state. However, serum is also known to contain factors that induce differentiation. Commercially available serum lots are routinely tested by users for their potential to keep ES cells in an undifferentiated state. Serum used for cES cell cultures are known to differ from serum used for mouse ES cell cultures. For example, serum used for the culture of mouse ES cells that is low in cytotoxin and hemoglobin concentration, which is known to maintain mouse ES cells in an undifferentiated state, did not support the sustained growth of chicken ES cells.

Therefore, serum to be used on chicken ES cells should not be tested on mouse ES cells to determine suitability as a media component, but instead should be evaluated on chicken ES cells. To do so, chicken ES cell cultures are divided into two and used to test each new batch of serum. The new batch tested must clearly support the growth of chicken ES cells when empirically tested.

Figure 3:
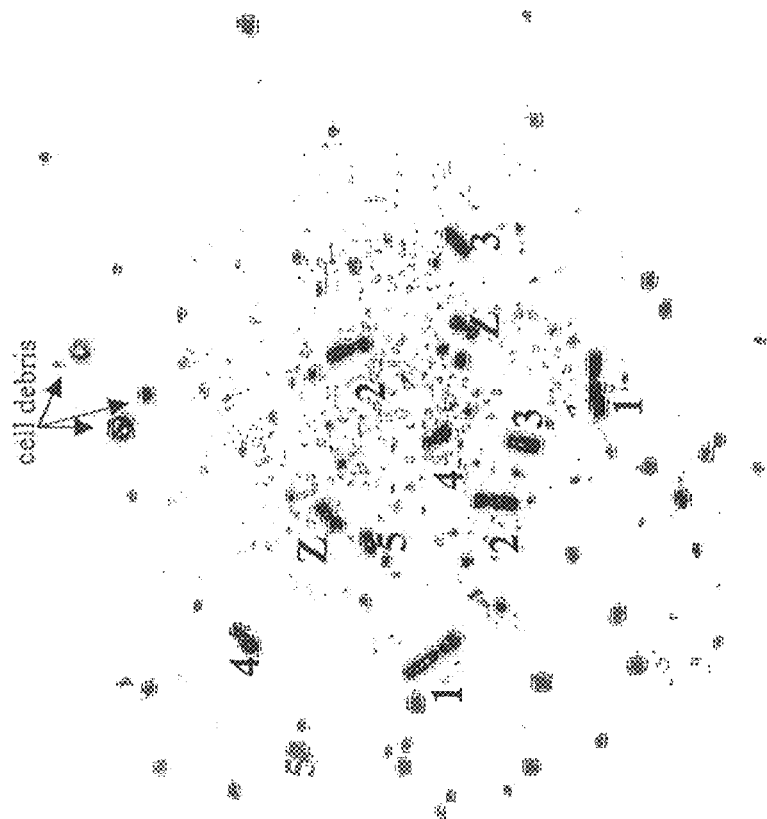
FIG. 3 is a karyotype of chicken ES cells that have been in culture for 189 days. The cells are diploid, carry 38 pairs of autosomal chromosomes and one pair of Z chromosomes.

Chicken chromosomal spreads require special evaluation techniques different than mice because the complex karyotype consisting of 10 macrochromosomes, 66 micro-chromosomes and a pair of sex chromosomes (ZZ in males and ZW in females). The long-term cES cells of the present invention shown in FIG. 3 were analyzed after 189 days in culture and being cryopreserved twice. Referring to FIG. 3, they exhibited a normal karyotype with 10 macro chromosomes; 2 Z-chromosomes and 66 microchromosomes.

Chicken ES cells are cryopreserved in 10% DMSO in medium. After thawing and injecting several cell lines into recipient embryos, somatic chimeras are obtained, indicating that the cES cells maintain their developmental potential during the cryopreservation process.

Example 2

Injection of Chicken Embryonic Stem Cells into Recipient Embryos

To permit access to the embryo in a freshly laid egg the shell must be breeched, inevitably leading to a reduction in the hatch rate at the end of the 21-day incubation period. The convention was to cut a small hole (less than 10 mm diameter) in the side of the egg, through which the embryo was manipulated, and re-seal with tape, a glass cover slip, shell membrane or a piece of shell. Though relatively simple to perform, this "windowing" method caused embryonic mortality between 70 and 100%. Improved access to the embryo and increased survival and hatchability can be achieved if the embryo is transferred to surrogate eggshells for incubation to hatching using two different shells and a method (adapted from Callebaut) (Callebaut, Poult. Sci 60: 723-725, 1981) and (Rowlett, K. and K. Simkiss, J. Exp. Biol. 143: 529-536, 1989), which are specifically incorporated herein by reference with this technique, the mean hatch rate is approximately 41% (range 23-70%) with 191 chicks hatched from 469 cES-cell injected embryos.

Incubation of embryos following injection of donor ES cells into recipient embryos can be divided into two parts comprising System A and System B as described below:

System A covers the first three days of post-oviposition development. Fertile eggs containing the recipient embryos are matched with eggs 3 to 5 grams heavier. A 32 mm diameter window is cut at the pointed pole, the contents removed and the recipient embryo on the yolk, together with the surrounding albumen, is carefully transferred into the surrogate shell.

Cells are taken up in a sterile, finely tapered glass pipette connected to a mouth aspirator fitted with a 2 micron filter. The opening of the pipette can be from 50 to 120 microns in diameter and possesses a 30° spiked bevel. The embryo is visualized under low magnification and with blue light. Chicken ES cells are trypsinized into a single cell suspension and between approximately 2,000 and 26,000 cells and preferably about 20,000 cells, are injected into an embryo. The cells are gently expelled into the space either below or above the embryo, i.e. into the sub-embryonic cavity or between the apical surface of the area pellucida and the perivitelline layer (yolk membrane). Extra albumen collected from fresh fertile eggs is added and the shell sealed with Saran Wrap plastic film.

System B covers the period from day three to hatching. At day three of incubation the embryo has reached around stage 17 (H&H). Water has been transported from the albumen to the sub-embryonic cavity, causing the yolk to enlarge and become very fragile. The contents of the System A shell are very carefully transferred to a second surrogate shell (usually a turkey egg) 30 to 35 grams heavier than the original egg. Penicillin and streptomycin are added to prevent bacterial contamination and the 38 to 42 mm window in the blunt pole is sealed with plastic film. This larger shell allows for an artificial airspace. At day 18 to 19 of incubation the embryo cultures are transferred to tabletop hatchers for close observation. As lung ventilation becomes established, holes are periodically made in the plastic film to allow ambient air into the airspace. Approximately 6-12 hours before hatching the film is replaced with a small petri dish, which the chick can easily push aside during hatching.

For incubation, conventional temperature (37.5 to 38° C.) and relative humidity (50 to 60%) are maintained for the embryos in surrogate shells, but periodic egg rocking, which is normally hourly and through 90 degrees, has to be modified to ensure good survival. In System A rocking is through 90° every 4 to 5 minutes; in System B it is through 40 to 60° every 40 to 45 minutes. In both systems the speed of rocking is maintained at 15 to 20° per minute.

Figure 4:
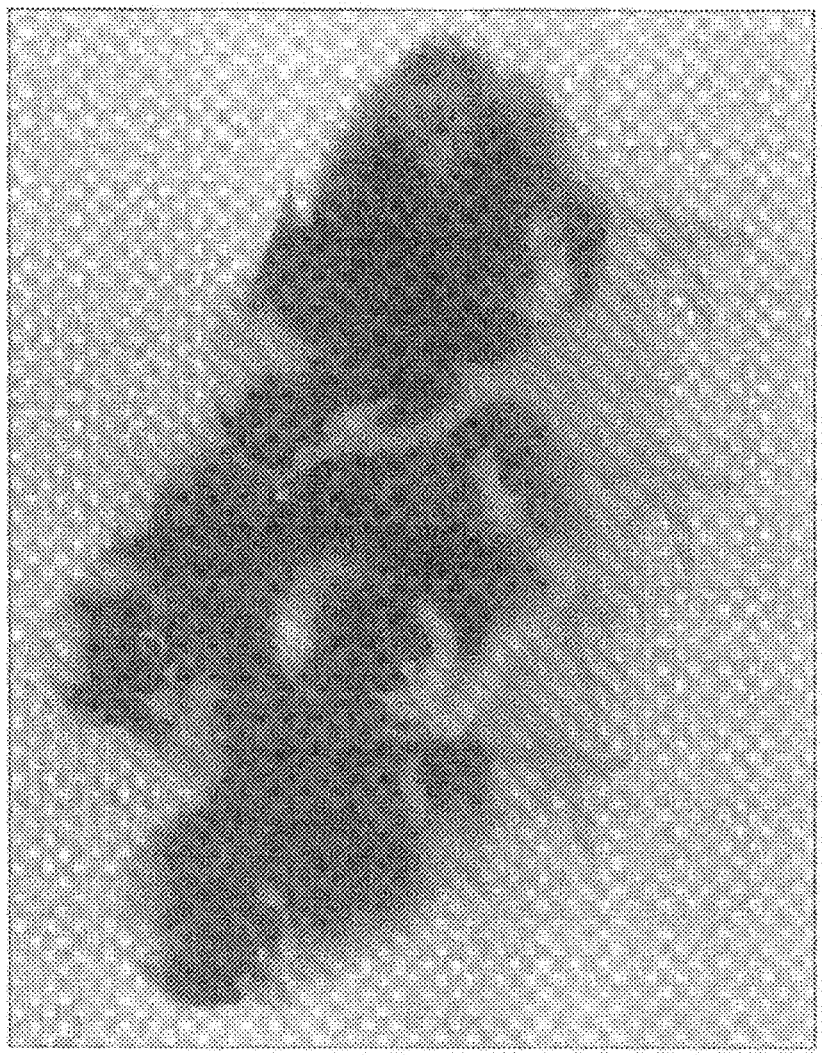
FIG. 4 is two Barred Rock chicks and two chimeras formed by injecting Barred Rock ES cells into a White Leghorn recipient embryo. The chimeras and the Barred Rocks are indistinguishable indicating that the contributions of the ES cells to the melanocyte lineage is extensive.

The contribution of cES cells to chimeras is improved if the recipient embryo is prepared by (1) irradiated by exposure to 660 rads of gamma irradiation (2) altered by mechanically removing approximately 1000 cells from the center of the embryo, or by combining (1) and (2) above before the injection of the cES cells. Referring to Table 5, contribution of cES cells to the somatic tissues increased substantially when recipient embryos were compromised, either by removing cells from the center of the recipient embryo or by exposure to irradiation. When the recipient embryos are compromised by a combination of irradiation and mechanical removal of the cells, the contribution of the ES cells is increased further, even though the cES cells had been in culture for longer periods of time. Some of the resulting chimeric chicks are indistinguishable from pure Barred Rock chicks (FIG. 4). As the data in Table 5 show, chimerism rates as well as the extent of chimerism per embryo increases after compromising the recipient embryo.

TABLE 5

Frequency of somatic chimerism after injection of cES cells into recipient embryos that were compromised by different methods.

| Treatment to compromise the recipient embryo | # Cell lines | Time cells in culture | # Chimeras | # Embryos & chicks evaluated | Frequency of chimerism % | Extent feather chimerism (%) |
|---|---|---|---|---|---|---|
| None | 14 | 4-106 days | 83 | 347 | 24 | 26 |
| Mechanical removal of cells | 1 | 6 months | 34 | 63 | 54 | 20 |
| Irradiation | 1 | 6-7 months | 56 | 95 | 59 | 29 |
| Irradiation & Mechanical removal of cells | 1 | 7-8 months | 52 | 59 | 88 | 49 |

Recipient embryos substantially younger than stage X may also be used to produce chimeras using ES cell as the donor. Early stage recipient embryos are retrieved by injecting the hens with oxytocin to induce premature oviposition and fertile eggs are retrieved at stages VII to IX.

Alternatively, the retrieval of embryos from the magnum region of the oviduct provides access to stage I to VI embryos, consisting of approximately 4-250 cells, and enables the development of chimeras from all embryonic stages as potential recipient embryos.

Example 3

Somatic Chimeras from Chicken Embryonic Stem Cells (cES)

Chicken ES cells are injected into White Leghorn recipient embryos. In the first round of experiments, a total of 14 cell lines in 28 experiments are injected into stage X recipient embryos (See Table 2). The cES cells have been propagated in culture between 4 and 106 days and some lines had been cryopreserved. Chicken ES cells are lightly trypsinized, resulting in small clumps of cES cells, and resuspended in DMEM supplemented with 25 mM HEPES+10% fetal calf serum. Three to five μl of the cell suspension, containing between 2000-5000 cells, are injected into the subgerminal cavity of the recipient embryos. All embryos that developed feathers are analyzed and twenty four percent of embryos (83/347) are chimeric as determined by feather color. Feather chimeras are obtained from 11/14 cell lines. The extent of chimerism varied from 1%-95% with a mean extent of 25.9% (SD=20.4).

Table 2 illustrates the variance in the somatic chimerism between experiments performed within and between cell lines. Examples of the contribution of ES cells to chimeras is shown in FIGS. 4 and 5. In FIG. 4, two chicks are chimeras and two are Barred Rocks; it is apparent that there are no phenotypic differences between these chicks indicating that the contribution of ES cells to the chimera is extensive, particularly in the ectodermally derived lineages. In FIG. 5, the chimeras on the left have relatively low levels of contribution from ES cells whereas those on the right have intermediate contributions.

Example 4

Transfection of cES Cells by Lipofection and Electroporation

Referring to Table 6, an appropriate amount of DNA compatible with the size of the well being transfected is diluted in media absent of serum or antibiotics. The appropriate volume of Superfect (Stratagene) is added and mixed with the DNA, and the reaction is allowed to occur for 5-10 minutes. The media is removed and the wells to be transfected are washed with a Ca/Mg free salt solution. The appropriate volume of media, which can contain serum and antibiotics, is added to the DNA/superfect mixture. The plates are incubated for 2-3 hours at 37 C. When the incubation is completed, the Superfect is removed by washing the cells 1-2× and fresh culture media is added.

TABLE 6

Conditions for transfection of chicken ES cells using Superfect.

| Plate Size | Volume of media used to dilute DNA | Total amount of DNA | ul Superfect | Time to form complex (min) | Volume of media added to complex | Incubation time |
|---|---|---|---|---|---|---|
| 96 well | 30 ul | 1 | 5 ul | 5-10 | 150 | 2-3 hrs |
| 48 well | 50 ul | 1.5 | 9 ul | 5-10 | 250 ul | 2-3 hrs |
| 24 well | 60 ul | 2 | 10 ul | 5-10 | 350 ul | 2-3 hrs |
| 12 well | 75 ul | 3 | 15 ul | 5-10 | 400 ul | 2-3 hrs |
| 6 well | 100 ul | 4 | 20 ul | 5-10 | 600 ul | 2-3 hrs |
| 60 mm | 150 ul | 10 | 50 ul | 5-10 | 1000 ul | 2-3 hrs |
| 100 mm | 300 ul | 20 | 120 ul | 5-10 | 3000 ul | 2-3 hrs |

A petri-pulser is used to electroporate cES cells that are attached to the plate in a 35 mm diameter well. The media is removed and the well is washed with a salt solution without $Ca^{++}$ and $Mg^{++}$. One ml of electroporation solution is added to the well. DNA is added and the media is gently mixed. The petri-pulser is lowered onto the bottom of the well and an electrical current is delivered. (Voltage preferably varies from 100-500 V/cm and the pulse length can be from 12-16 msec). The petri-pulser is removed and the electroporated well is allowed to stand for 10 minutes at room temperature. After 10 minutes, 2 mls of media is added and the dish is returned to the incubator.

To transfect cells in suspension, media is removed and cells are washed with a Ca/Mg free salt solution. Tryspin with EDTA is added to obtain a single cell suspension. Cells are washed, centrifuged and resuspended in a correctional electroporation buffer solution such as PBS. The ES cell suspension is placed into a sterile cuvette, and DNA added (minimum concentration of 1 mg/ml) to the cell suspension and mixed by pipetting up and down. The cells are electroporated and allowed to sit at RT for 10 minutes. Cells are removed from cuvette and distributed to previously prepared wells/dishes. Cells are placed in an incubator and evaluated or transient transfection 24-48 hours after electroporation. Selection of antibiotic resistant cells may also be started by including an antibiotic such as puromycin in the culture medium.

In a preferred embodiment, the concentration of puromycin required for selecting transfected cells is calculated as a titration kill curve. Titration kill curves for chicken embryonic stem cells are established by exposing cells in culture to puromycin concentrations varying from 0.0 to 1.0 μg/ml for 10 days (Table 7) and neomycin concentrations varying from 0.0 to 200 μg/ml (Table 8). The medium is changed every 2 days and fresh puromycin or neomycin is added. When exposed to a concentration of 0.3 μg/ml puromycin, ES cells were absent from all wells after 3 changes of medium with fresh puromycin over a six day period (see Table 7). Puromycin concentrations of 0.3-1.0 μg/ml are used for selection of the transfected cultures. Neomycin concentrations over 40 μg/ml eliminated all cES cells within 7 days (Table 8).

After 10 days of selection, cES cells colonies are visible and can be picked for further expansion.

TABLE 7

Morphology of cES cells after exposure of various concentrations of puromycin and different lengths of time (days after addition of puromycin).

| Puromycin conc. | Time under selection (days) | | | | | | | | | |
|---|---|---|---|---|---|---|---|---|---|---|
| (μg/ml) | 1 | 2 | 3 | 4 | 5 | 6 | 7 | 8 | 9 | 10 |
| 0.0 | ES | ES | ES | ES | ES | ES | ES | ES | ES | ES |
| 0.1 | ES | ES | ES | ES | ES | ES | ES | ES | ES | ES |
| 0.2 | ES | ES | ES | ES | ES | ES | ES | ES | ES | ES |
| 0.25 | ES | ES | ES | ES | ES | diff | diff | diff/gone | diff/gone | diff/gone |
| 0.3 | ES | ES | diff | diff/gone | diff/gone | gone | gone | gone | gone | gone |
| 0.4 | ES | diff | gone | gone | gone | gone | gone | gone | gone | gone |
| 0.5 | diff | gone | Gone | gone | gone | gone | gone | gone | gone | gone |
| 0.6 | diff | gone | gone | gone | gone | gone | gone | gone | gone | gone |
| 0.7 | diff | gone | gone | gone | gone | gone | gone | gone | gone | gone |
| 0.8 | gone | gone | gone | gone | gone | gone | gone | gone | gone | gone |

ES: ES cells are present.
diff: ES cells are differentiated.
gone: no morphologically recognizable cells are present

TABLE 8

Morphology of cES cells after exposure of various concentrations of neomycin and different lengths of time (days after addition of neomycin).

| Neomycin conc. | Time under selection (days) | | | | | | | | | |
|---|---|---|---|---|---|---|---|---|---|---|
| (μg/ml) | 1 | 2 | 3 | 4 | 5 | 6 | 7 | 8 | 9 | 10 |
| 0.0 | ES | ES | ES | ES | ES | ES | ES | ES | ES | ES |
| 10 | ES | ES | ES | ES | ES | ES | ES | ES | ES | ES |
| 20 | ES | ES | ES | ES | ES | ES | ES | ES | ES | ES |
| 30 | ES | ES | ES | ES | ES | ES | ES/Diff | ES/diff | Diff | Diff/gone |
| 40 | ES | ES | ES | ES | ES/Diff | Diff/dead | dead | gone | gone | gone |
| 50 | ES | ES | ES | ES/Diff | ES/Diff | Diff/dead | Dead/gone | gone | gone | gone |
| 60 | ES | ES | ES | gone | gone | gone | gone | gone | gone | gone |
| 100 | ES/Diff | Diff | dead | gone | gone | gone | gone | gone | gone | gone |
| 150 | | dead | dead | gone | gone | gone | gone | gone | gone | gone |
| 200 | | dead | gone | gone | gone | gone | gone | gone | gone | gone |

Example 5

Tissue Specific Antibody Expression

Depending on the design of the transgene, DNA encoding an exogenous antibody is designed to express significant levels of antibody only in a selected tissue. The transgene construct may be comprised of genetic elements derived from the genome of the host organism and selected on the basis of known expression, or patterns of expression, of an antibody in a selected tissue. For expression in a particular tissue, a gene encoding a protein that is normally expressed, and usually highly expressed in the selected tissue, is selected and regulatory elements from the gene are chosen to drive expression of the exogenous antibody. When combined with DNA coding sequences for the exogenous antibody, other regulatory elements, such as the ovalbumin, ovotransferrin, ovomucoid, ovomucin, lysozyme, ovoglobulin, ovoinhibitor, cystatin, ovoglycoprotein, ovoflavoprotein, ovomacroglobulin, or avidin promoters, in combination with genes encoding selectable markers, and/or in combination with an IRES may be used. The transgene yields preferential expression of the antibody in the selected tissue, preferably in egg white. Preferential expression in a specific tissue type may be defined as 3 to 4 orders of magnitude greater expression in the selected tissue in comparison to non-selected tissues.

For tissue specific antibody expression in a transgenic bird, the tissue specific expression is preferably directed to a region of the oviduct including the magnum, isthmus, shell gland, or infundibulum. The magnum contains the tubular gland cells that express the predominant proteins of the egg white, while the isthmus contains cells that express the shell membrane. Soluble protein expression is preferably directed to the tubular gland cells of the magnum of the oviduct by selecting regulatory sequences, usually comprising a promoter, from genes expressing egg white proteins, preferably ovalbumin, but including ovotransferrin, ovomucoid, lysozyme, ovoglobulin G2, ovoglobulin G3, ovoinhibitor, cystatin, ovoglycoprotein, ovoflavoprotein, ovomacroglobulin, and avidin. Selective expression in the tubular gland cells, to the exclusion of expression in the epithelial cells is demonstrated below and termed preferential expression to distinguish selectivity between the two cell types.

In the following example, a transgene containing an endogenous egg white regulatory sequence comprising a promoter together with an exogenous immunoglobulin locus is constructed to yield tissue specific antibody expression in the tubular gland cells of the oviduct. The antibody molecules so expressed are then deposited in the egg white of a transgenic chicken. In this embodiment, antibodies encoded by any rearranged immunoglobulin gene are expressed specifically in tissue comprising the tubular gland cells of the magnum region of the oviduct and can be isolated from the whites of eggs. The rearranged immunoglobulin gene encoding a monoclonal antibody is preferentially expressed in the oviduct to the substantial exclusion of expression in other tissues, although expression in other tissues may exist above detectable levels.

In this embodiment, the monoclonal antibody cassette under the control of the ovalbumin regulatory sequences is comprised of at least 3.4 kb and preferably at least approximately 7.5 kb of the 5' regulatory sequence and may include 15 kb or more of the 3' regulatory sequence. Preferably, the construct includes regions of the ovalbumin gene flanking both the 5' and 3' ends of the exogenous antibody coding region although a large enough segment of the endogenous promoter sequence of the 5' flanking region may avoid the need for a 3' flanking region. The coding regions of both the heavy and light chains of the antibody are provided in the transgene and include the variable, diversity; joining and constant regions of the selected isotype. In a preferred embodiment, the antibody is encoded by an immunoglobulin gene that is characteristically human and contains at least a human heavy chain. Also, the isotype is preferably IgG, and most preferably IgG1.

Figure 6A:
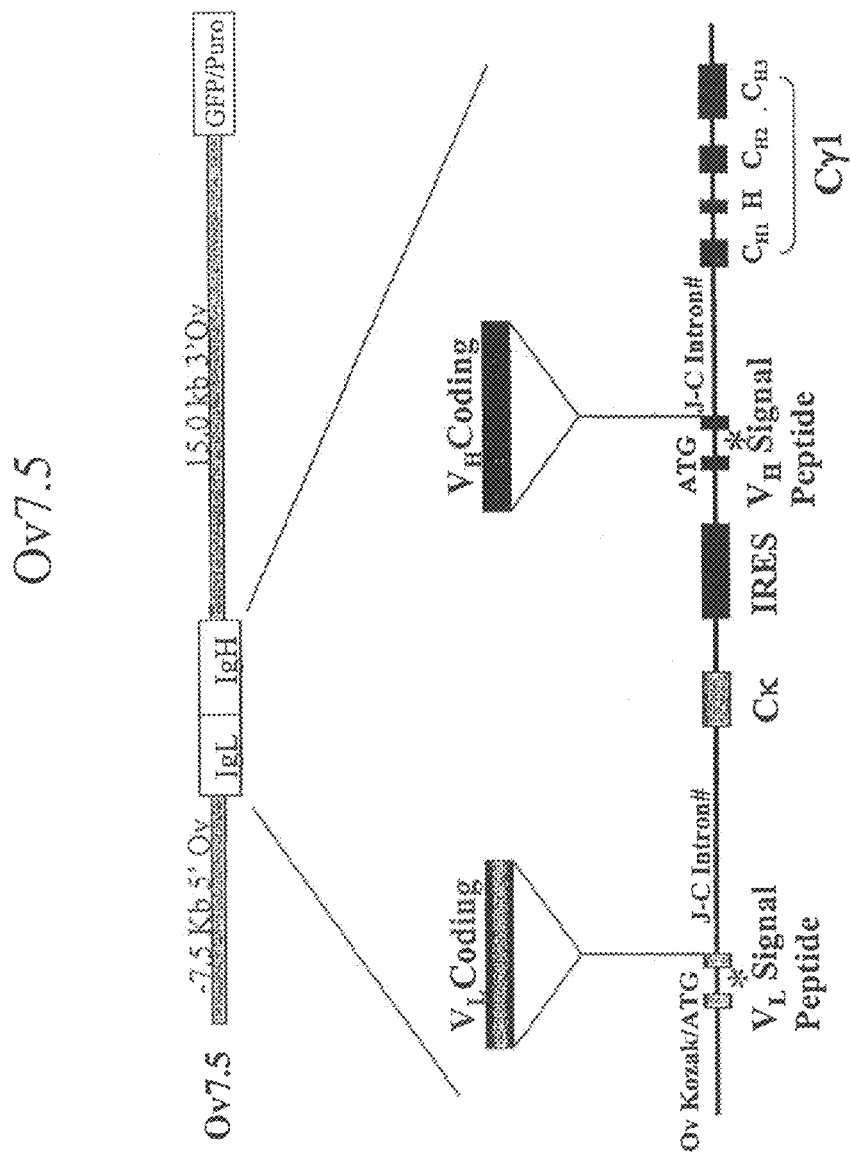

A preferred transgene construct for an ovalbumin derived monoclonal antibody construct is provided in FIG. 6A. This transgene construct is designated Ov7.5 and has approximately 7.5 kb of an egg white regulatory sequence comprising a promoter, in this specific embodiment the ovalbumin promoter, flanking the MAb coding at the 5' end sequence and 15 kb of the promoter sequence 3' of the coding region. The coding regions comprise the variable regions for both the light chain and heavy chain, J-C intron sequences, the kappa light chain constant region, an IRES sequence and the gamma 1 isotype heavy chain constant regions. The 3' end of the construct comprises a GFP gene and a selectable marker, in this case a puromycin resistance gene driven by the CX promoter described herein. The lengths of the ovalbumin promoter sequence both 3' and 5' of the monoclonal antibody coding region are examples only and analogous constructs may include 25-100 kb or more of the 5' sequence as well as varying lengths in the 3' sequence. Those of ordinary skill in the art will appreciate that the GFP marker is present only for detection in physiological specimens and can be removed without departing from the utility of the transgene. The puromycin resistance marker can be substituted with any marker that provides the ability to select embryonic stem cells that are successfully transformed with the transgene. Several types of analogous selectable marker are well known in the art and can be used essentially interchangeably with the puromycin resistance gene of this embodiment.

As noted above, this monoclonal antibody is only one example of several types of monoclonal antibody products that may be expressed using the transgene constructs of the invention. Moreover, monoclonal antibodies as a class of proteins are only one example of many classes of protein products that may be expressed in tissue-specific fashion pursuant to the methods and techniques described herein.

Referring to FIG. 6B, a section of the magnum of two-week old chimeras in which expression of the Ov 7.5 transgene was induced by estrogen injection shows tissue specific expression of the anti-dansyl monoclonal antibody producing cells derived from the transformed embryonic stem cell express GFP, which shows as green in the top left panel of FIG. 6B, confirm contribution by the embryonic stem cell transformed with the Ov 7.5 transgene. Referring to the bottom left panel of FIG. 6B, the monoclonal antibody stains red in the tubular gland cells, while the epithelial cells, which are also derived from the donor embryonic stem cell, stain green and do not stain red. This difference in staining demonstrates that expression of the construct is tissue specific and selected by the content of the transgene for the specific tissue type. While the example below demonstrates tissue specific expression in the tubular gland cells of the oviduct, the demonstration of expression across all cell and tissue types demonstrates that each or any tissue type could be chosen for tissue- or cell-specific expression by corresponding selection of the components of the transgene construct, and e.g. the promoter or other regulatory elements.

Figure 7A:
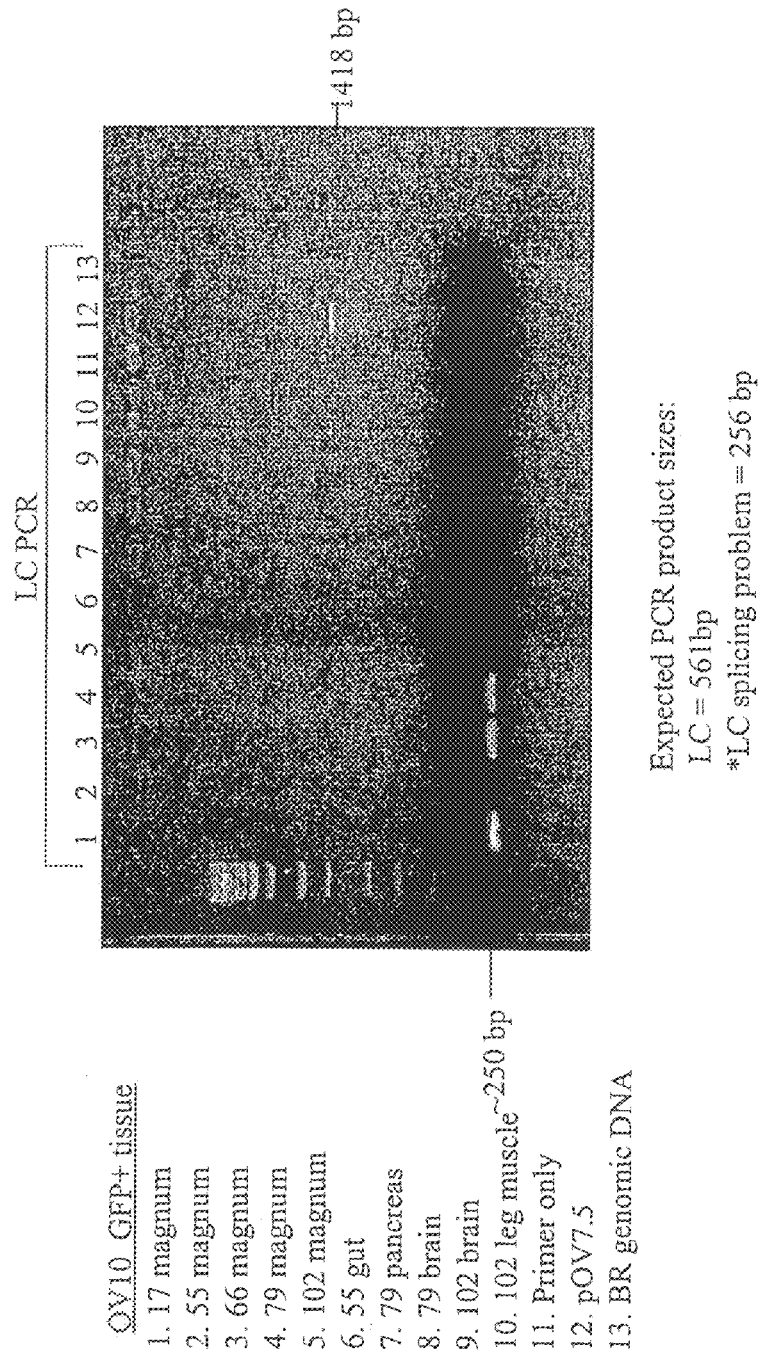
FIGS. 7A and 7B are RT-PCR analyses showing expression of both the light and heavy chain, respectively, of a monoclonal antibody in the oviduct, to the exclusion of brain, gut, pancreas and muscle tissue of the chimeras.
Figure 7B:
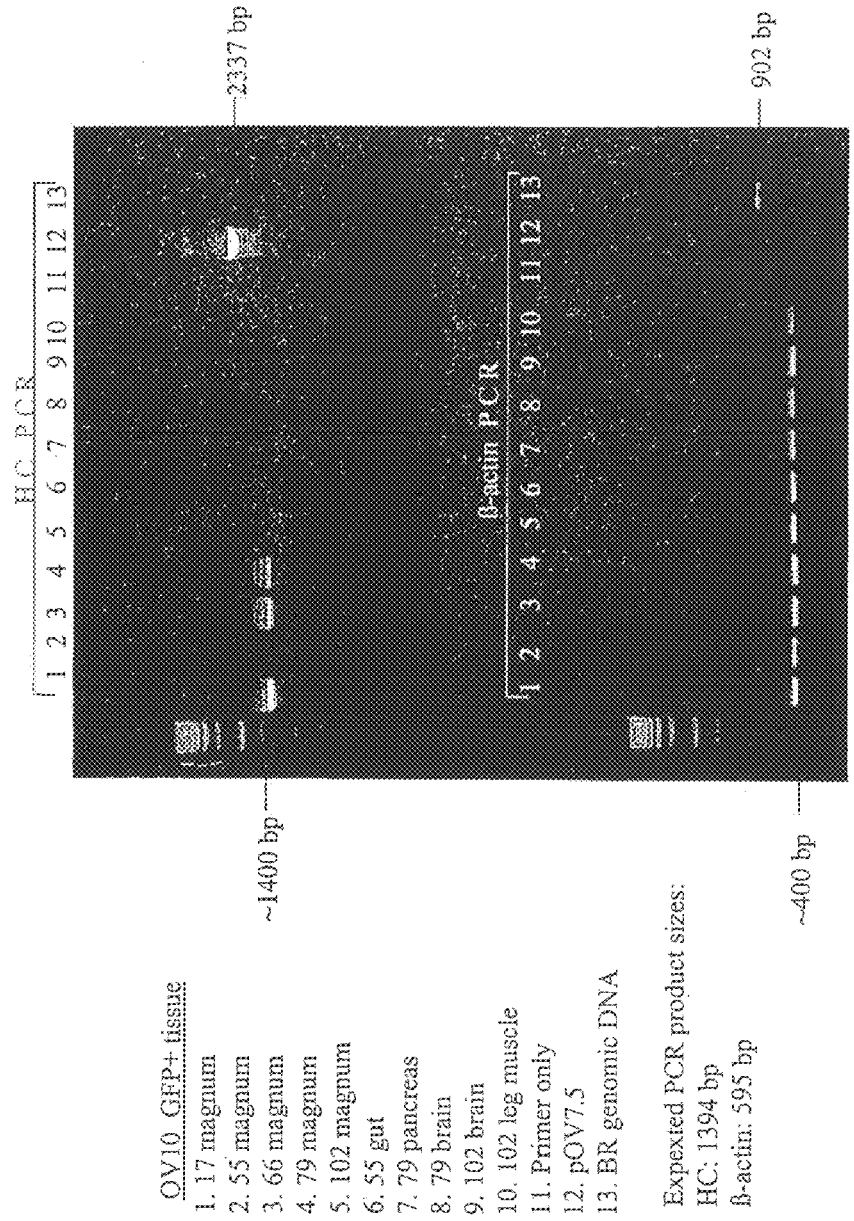

In the top right panel of FIG. 6B, all of the cell types are shown by DAPI staining. In the bottom right panel, the stains are overlaid to demonstrate that only donor-derived tubular gland cells express the monoclonal antibody, while recipient-derived cells and donor-derived epithelial cells do not express the monoclonal antibody. FIGS. 7C and 7D are RT-PCR analyses showing that the heavy chain and light chain, respectively, of the anti-dansyl monoclonal antibody are selectively expressed in only the oviduct tissue of 3 or 5 chimeras and not in the brain, gut, pancreas or muscle of these chimeras above levels detected by RT-PCR.

To demonstrate that a human IgG isotype monoclonal antibody could be selectively expressed and the protein deposited is egg white, a total of 18 chimeric females were produced by injecting cES cells carrying the Ov7.5 construct. Six chimeras from this group were used for testing transgene expression by early estrogen induction. The remaining 12 chimeric females were reared to sexual maturity for egg collection. Nine chimeric females commenced laying at 17-22 weeks of age and one of these chimeras laid sporadically. Three of the chimeric females had not laid eggs at 35 weeks of age and at autopsy it was evident that their gonad was masculinized by the presence of male ES cell derived tissue.

Eggs from the nine egg laying chimeras were collected and representative egg white samples were prepared by ammonium sulfate precipitation and analyzed by ELISA. The microtiter plates were coated with a goat anti-human IgG antibody and the presence of human IgG MAb in the egg white samples was revealed by either a labeled goat anti-human IgG (γ chain specific) antibody for heavy chain and/or a labeled goat anti-human kappa (κchain specific) antibody for light chain. The standard curves were established with purified human Igγ1, κ proteins. The sensitivity of the ELISA was 0.8 ng/ml. Egg white samples from non-transgenic White Leghorn hens were used as negative controls. No human IgG MAb deposition was detectable in eggs from non-transgenic White Leghorn hens (4 eggs) or from 6 chimeric hens (8 eggs from hen #OV11-17, 8 eggs from hen #OV11-53, 6 eggs from hen #OV11-73, 6 eggs from hen #OV11-88, 4 eggs from hen #OV12-97 and 5 eggs from hen #OV13-13).

Human IgG MAb deposition were detected in eggs from 3 different chimeric hens (~1.4-6.3 ng/ml for eggs from hen #OV11-13, ~2.0-2.9 ng/ml for eggs from hen #OV11-37 and ~2.9-10.8 ng/ml for eggs from hen #OV11-43 as determined by ELISA for IgH). The concentration of human IgG MAb in representative eggs is summarized in Table 9. The concentration of human IgG MAb in eggs determined by ELISA for IgL was consistently lower than that determined by ELISA for IgH. In general, the concentration determined by IgL was 60% of the concentration determined by IgH (compare columns 3 and 5 in Table 9). The difference was also present in spiked samples made with purified human Igγ1, κ proteins.

TABLE 9

Deposition of human IgG MAb in eggs from chimeras

| Egg ID | Date laid | Human IgG level by IgH ELISA (ng/ml)* | Corrected IgG value in egg white (ng/ml)** | Human IgG level by IgL ELISA (ng/ml)* |
|---|---|---|---|---|
| OV11-43-9 | Nov. 12, 2002 | 7.6 | 10.8 | 4.6 |
| OV11-43-10 | Nov. 13, 2002 | 5.2 | 7.4 | 3.4 |
| OV11-43-11 | Nov. 14, 2002 | 6.8 | 9.7 | 4.2 |
| OV11-43-13 | Nov. 17, 2002 | 5.4 | 7.7 | 3.4 |
| OV11-43-14 | Nov. 18, 2002 | 4.6 | 6.6 | 3.2 |
| OV11-43-25 | Nov. 30, 2002 | 3.0 | 4.3 | 1.8 |
| OV11-43-26 | Dec. 01, 2002 | 2.0 | 2.9 | 1.2 |
| OV11-43-33 | Dec. 08, 2002 | 7.0 | 10.0 | 4.2 |
| OV11-13-1 | Nov. 24, 2002 | 3.6 | 5.1 | 2.4 |
| OV11-13-2 | Nov. 26, 2002 | 4.4 | 6.3 | 2.6 |
| OV11-13-3 | Dec. 2, 2002 | 3.8 | 5.4 | 2.4 |
| OV11-13-4 | Dec. 10, 2002 | 2.6 | 3.7 | 1.4 |
| OV11-13-5 | Dec. 11, 2002 | 3.6 | 5.1 | 2.2 |
| OV11-13-11 | Dec. 17, 2002 | 3.2 | 4.6 | 2.2 |
| OV11-13-37 | Jan. 27, 2003 | 1.0 | 1.4 | ~0.6 |
| OV11-37-1 | Dec. 08, 2002 | 2.0 | 2.9 | 1.2 |
| OV11-37-2 | Dec. 11, 2002 | 2.0 | 2.9 | 1.2 |
| OV11-37-3 | Jan. 06, 2003 | 1.4 | 2.0 | ~0.6 |

*Some egg white samples were prepared and assayed multiple times and the values were averaged.
**The recovery for sample preparation was estimated at 50-70% using negative control egg white samples spiked with known amount of purified human Igγ1, κ proteins. The IgG value given in Column 4 was corrected based on a recovery of 70% for sample preparation to provide a conservative estimate of the concentration of human Ig in egg white.

The concentration of human IgG MAb proteins in blood samples from hens #OV11-13, #OV11-37 (which deposited the human Ig in their eggs) and a White Leghorn was less than the sensitivity of the assay (0.8 ng/ml). These data are consistent with the absence of ectopic expression of human Ig in chimeric chickens that was observed using RT-PCR to evaluate the presence of the human Ig transcripts in gut, brain, pancreas and muscle in estrogen induced chimeric chicks (FIGS. 7C and D). The Ov7.5 construct, therefore, appears to deliver tissue specific, hormonally induced and developmentally regulated gene expression in transgenic chimeric hens. Furthermore, the protein appears to be exported from the tubular gland cells in the magnum and deposited in egg white.

The ovalbumin-derived tissue specific protein expression transgenes were constructed as follows:

A chicken genomic BAC library (Crooijmans, R. P. et al., Mamm. Genome 11: 360-363, 2000), (Texas A & M BAC Center) is screened to isolate a region of 46 Kb in the ovalbumin locus. Two different vectors were constructed having different fragments of the ovalbumin promoter located 5' of the MAb coding region: (1) Ov7.5MAb-dns: A 42 Kb expression vector contains 9.2 Kb 5' sequences from the ovalbumin gene (including 7.5 Kb promoter) and 15.5 Kb 3' flanking sequences (FIG. 10A). This 42 kb expression vector contains 9.2 kb of 5' sequence from the ovalbumin gene (including 7.5 kb promoter) and 15.5 kb 3' flanking sequences. A bicistronic monoclonal antibody cassette encodes the light chain, an IRES and the heavy chain of an anti-dansyl antibody. (2) Ov15MAb-dns: A 49 Kb expression vector contains 16.8 Kb 5' sequences from the ovalbumin gene (including 15 Kb promoter) and 15.5 Kb 3' flanking sequences (not shown). The 49 kb expression vector contains 16.8 kb of 5' sequence from the ovalalbumin gene (including 15 kb promoter) and 15.5 kb3' flanking sequences. The monoclonal antibody cassette is identical in both constructs.

As noted above, one example of a gene to be expressed in both vectors is a mouse-human hybrid anti-dansyl monoclonal antibody (MAbdns). The CxEGFP/CxPuro cassette is cloned in the most 3' end to allow selection with puromycin for stable transfection in cES cells and easy identification of transfected cells in chimeras. Both constructs are linearized and purified before transfection into cES cells. Transfections of cES cells are performed with Ov7.5MAbdns and Ov15MAb using either SuperFect (Stratagene) or petri-pulser electroporation. After selection with puromycin, 6 resistant clones are picked for molecular analysis. The presence of the transgene is confirmed by PCR with primers located in the MAbdns cassette, in the GFP gene and in the Puro gene.

A second example of an antibody to be expressed is a fully human anti-human PSMA monoclonal antibody (MAbF1). V genes corresponding to MAbF1 were obtained by PCR and used to replace the V genes in Ov15MAb-dns.

This transgene was stably incorporated into female ES cells and the stably transfected cells were injected into Stage X recipient embryos. The resulting chimeras were reared to sexual maturity and the concentration of the human monoclonal antibody in eggs was assessed by ELISA. Four of 30 hens deposited the antibodies in their eggs at concentrations in excess of 1 mg/egg (Table 9A).

TABLE 9A

Concentration of human IgG MAb in eggs from Ov15MAbF1 chimeras

| Mean of MAb/egg (mg) | Number of hens | Range of [MAb] in egg (□g/ml) | Range of MAb/egg (mg) |
|---|---|---|---|
| >1.0 | 4 | 34.6-147.9 | 0.7-3.4 |
| >0.5 to 1.0 | 6 | 9.0-61.6 | 0.2-1.4 |
| >0.1 to 0.5 | 7 | 3.3-23.2 | 0.1-0.6 |
| >0.01 to 0.1 | 13 | 0.2-5.4 | 0.01-0.1 |

The mean value of MAb/egg from each hen was an average of values from 2 to 10 eggs.

Example 6

Characterization of Antibody Product

The MAbF1 produced in chicken was compared in several assays with MAbF1 produced in conventional CHO cell culture.

1. SEC-HPLC Analysis of Antibody

About 10μγ of IgG sample was analyzed on a Waters 2795 HPLC using a 4.6×300 mm BioSep SEC S3000 column (Phenomenex). Chromatography was carried out in 0.1 M sodium phosphate, 0.15 M NaCl, and 0.1 M sodium sulfate, pH 7.2 at 0.4 ml/min flow rate for 20 min. Separations were monitored at $A_{280}$. Molecular weight standards (Bio-Rad) were used to determine approximate molecular weight. The SEC-HPLC analysis showed that both were more than 90% IgG monomer (Table 10).

TABLE 10

SEC-HPLC analysis of MAbF1

| Antigen | Clone | IgG Monomer (% peak area) | IgG Aggregate (% peak area) | IgM (% peak area) |
|---|---|---|---|---|
| PSMA | MAbF1 CHO | 97.2 | 2.8 | 0.0 |
| PSMA | MAbF1 Chicken | 100.0 | 0.0 | 0.0 |

2. Nano LC ESI MS/MS Analysis of Protein

Both MAb preparations were reduced and alkylated, dialyzed overnight and digested with trypsin for 4 hours at 37° C. in 25 mM ammonium bicarbonate (PH 8). Tandem mass spectrometry of both tryptic digests was performed on a Nano HPLC system (Dionex, Sunnyvale, Calif.) interfaced to a QSTAR pulsar mass spectrometer (MDS Sciex, Concord, Ontario, Canada) operation in positive ion mode and using collision induced dissociation (CID) to obtain tandem spectra. A μl 1 ml aliquot of each sample was injected and separated using a 75 mm diameter μm Pepmap C18 column at a flow rate of 250 nl/min. The mobile phase was solvent A (95% water, 5% acetonitrile, 0.5% formic acid) and solvent B (20% water, 80% acetonitrile, 0.5% formic acid). The instrument was operated in information dependent acquisition mode with 7 s operating cycles, recording a full spectrum for 2 s then selecting the most intense ion to record a CID spectrum during the next 5 s. Spectra were analyzed using Mascot (Matrix Science, London, UK). Analysis of both MAb preparations by the described methods showed no sequence difference.

TABLE 11

Sequence analysis of chicken produced and CHO produced MAbF1 by mass spectrometry

| Peptide | Location | Theoretical mass | Observed mass in CHO HuMAb (Da) | Observed mass in Chicken HuMAb (Da) | Sequence (SEQ ID NO.) |
|---|---|---|---|---|---|
| T1 | 1-12 | 1227.68 | 1227.69* | 1227.68* | AVQLVQSLGAEVK (1) |
| T1 | 1-19 | 1967.10 | 1967.12 | 1966.90 | AVQLVQSLGAEVKKPGESLK (2) |
| T4 | 24-38 | 1720.79 | 1720.67 | 1721.08 | GSGYSFT SFWIGWAR (3) |
| T4-T5 | 24-43 | 2262.02 | 2262.78 | 2259.9 | GSGYSFT SFWIGWARQMPGK (4) |
| T6 | 44-59 | 1808.84 | 1808.74 | 1808.73 | PGKGLEWMGI IYPGDSDTR (5) |
| T7 | 60-74 | 1626.78 | 1626.70 | 1626.69 | YSPSFQGQVTI SADK (6) |
| T8 | 75-87 | 1482.77 | 1482.93 | 1482.77 | SISTAYLQVVSSLK (7) |
| T10 | 112-123 | 1149.62 | 1149.57* | 1149.54 | GTLVTVSSASTK (8) |
| T11 | 124-135 | 1185.63 | 1185.60* | 1185.60* | GPSVFPLAPSSK (9) |
| T12 | 136-149 | 1263.64 | — | 1263.5* | STSGGTAALGCLVK (10) |
| T15-17 | 216-224 | 1060.55 | — | 1060.41 | RVEPKSCDK (11) |
| T16 | 217-220 | 470.21 | — | 471.22 | VEPK (12) |

TABLE 11-continued

Sequence analysis of chicken produced and CHO produced MAbF1 by mass spectrometry

| Peptide | Location | Theoretical mass | Observed mass in CHO HuMAb (Da) | Observed mass in Chicken HuMAb (Da) | Sequence (SEQ ID NO.) |
|---|---|---|---|---|---|
| T17 | 221-224 | 508.20 | — | 508.23 | SCDK (13) |
| T19 | 251-257 | 834.33 | 834.43* | 834.31 | DTLMISR (14) |
| T19 | 251-257 | 850.31 | 850.42* | — | DTLM(ox)ISR (15) |
| T20 | 258-276 | 2080.99 | 2080.99 | 2081.78 | TPEVTCVVVDVSH EDPEVK (16) |
| T21 | 277-290 | 1676.79 | 1676.65 | 1676.74 | FNWY VDGVEVHNAK (17) |
| T22-t23 | 291-303 | 1670.80 | — | 1670.83 | TKPREEQYNSTYR (18) |
| T24 | 304-319 | 1806.99 | 1807.21 | 1806.97 | VVSVLTVLHQDWLNGK (19) |
| T27-t28 | 325-336 | 1265.73 | 1265.70* | 1265.61 | VSNKALPAPIEK (20) |
| T28 | 329-336 | 837.49 | 837.49 * | 837.49* | ALPAPIEK (21) |
| T29 | 337-346 | 1084.63 | 1084.42 | — | TISKAKGQPR (22) |
| T32 | 347-357 | 1285.66 | — | 1285.67* | EPQVYTLPPSR (23) |
| T32-33 | 347-362 | 1871.98 | — | 1871.97 | EPQVYTLPPSRDELTK (24) |
| T34 | 363-372 | 1103.60 | — | 1103.49* | NQVSLTCLVK (25) |
| T34 | 363-372 | 1160.49 | 1160.62* | 1160.62* | NQVSLTC(carb)LVK (26) |
| T35 | 373-394 | 2543.12 | — | 2543.15 | GFYPSDIAVEWESNGQPENNYK (27) |
| T36 | 395-411 | 1872.91 | 1872.77 | 1872.65 | TTPPVLDSDGSFFLYS KLTVDK (28) |
| T37 | 412-416 | 574.30 | 574.33 | — | LTVDK (29) |
| T41 | 450-467 | 1897.02 | 1897.10* | 1896.76* | EIVLTQSPATLSLSPGER (30) |
| T43 | 474-494 | 2351.16 | 2351.17* | 2350.93* | ASQSVSSYLAWYQQKPGQAPR (31) |
| T44 | 495-503 | 1063.56 | 1063.52* | 1063.50* | LLIYDASNR (32) |
| T44-T45 | 495-510 | 1729.94 | — | 1730.45 | LLIYDASNRATGIPAR (33) |
| T47 | 541-553 | 1531.71 | 1531.54 | 1531.50 | SNWLMYTFGQGTK (34) |
| T48-T50 | 554-576 | 2584.42 | — | 2583.05 | LEIKRTVAAPSVFIFPPSDEQLK (35) |
| T49-T50 | 558-576 | 2101.12 | — | 2101.09 | RTVAAPSVFIFPPSDEQLK (36) |
| T50 | 559-576 | 1945.01 | — | 1944.9 | TVAAPSVFIFPPSDEQLK (37) |
| T51 | 577-592 | 1739.86 | 1740.76 | 1739.52 | SGTASVVCLLNNFYPR (38) |
| T54 | 600-619 | 2134.96 | — | 2134.94 | VDNALQSGNSQESVTEQDSK (39) |
| T55 | 620-633 | 1501.75 | 1501.73* | 1501.74 | DSTYSLSSTLTLTLSK (40) |
| T58-T60 | 641-664 | 2611.21 | — | 2612.96 | VYACEVTHQGLSSPVTKSFNRGEC (41) |

*Indicates that the information is further confirmed by MS sequencing in addition to peptide mapping; ox, oxidation; carb, carbamidomethylation. T1-T37 are from H chain, and T41-T60 are from L chain.

3. LC-MS Analysis

IgG samples (50μγ) in 4 M guanidine HCl were reduced in 25 mM DTT by incubating the samples at 60° C. for 90 min. Samples were then alkylated in 45 mM iodoacetic acid for 15 min at room temperature in the dark and the reaction was stopped with 22 mM DTT. Prior to LC-MS samples were dialyzed against 1 L of 25 mM ammonium bicarbonate and 50 μl of each sample was injected to a Poros R1/10 2.1×100 mm column (Applied Biosystems) using a Waters 2795 HPLC equipped with a Micromass ZQ mass spectrometer and analyzed in positive ion mode. The mobile phase was (A) 0.1% formic acid and 0.01% trifluoroacetic acid (TFA) and (B) 100% $CH_3CN$ with 0.1% formic acid and 0.01% TFA. Elution (0.25 ml/min) was conducted by a linear gradient of 10-60% of (B) in (A) developed over 100 min.

Analysis of the L chain showed that both MAb preparations had identical mass (+/−3 Da.) (Table 12)

TABLE 12

LC-MS analysis of MAb light chain

| Antigen | Clone | Observed Mass (Dalton) | Relative Abundance (%) |
|---|---|---|---|
| PSMA | MAbF1 CHO | 23,904 | 100 |
| PSMA | MAbF1 Chicken | 23,903 | 100 |

4. Thermal Stability by Differential Scanning Calorimetry

The thermal stabilities of MAbF1 produced in the chicken and CHO expression systems were obtained using differential scanning calorimetry (DSC) and compared with their corresponding forms that were deglycosylated in their Fc domain. Calorimetric measurements of melting temperatures ($T_m$) were carried out on a VP-Capillary DSC differential scanning microcalorimeter platform that is combined with an autosampler (MicroCal LLC, Northampton, Mass., USA). Sample cell volume is 0.144 mL. Denaturation data on the glycosylated and deglycosylated forms of the antibodies was obtained by heating the samples, at a concentration of 2.3 µM, from 30 to 95° C. at a rate of 1° C./min. The protein samples were present in phosphate-buffered saline (PBS) at pH 7.4. The same buffer was used in the reference cell to obtain the molar heat capacity by comparison. The observed thermograms were baseline corrected and normalized data was analyzed using Origin v7.0.

Figure 8:
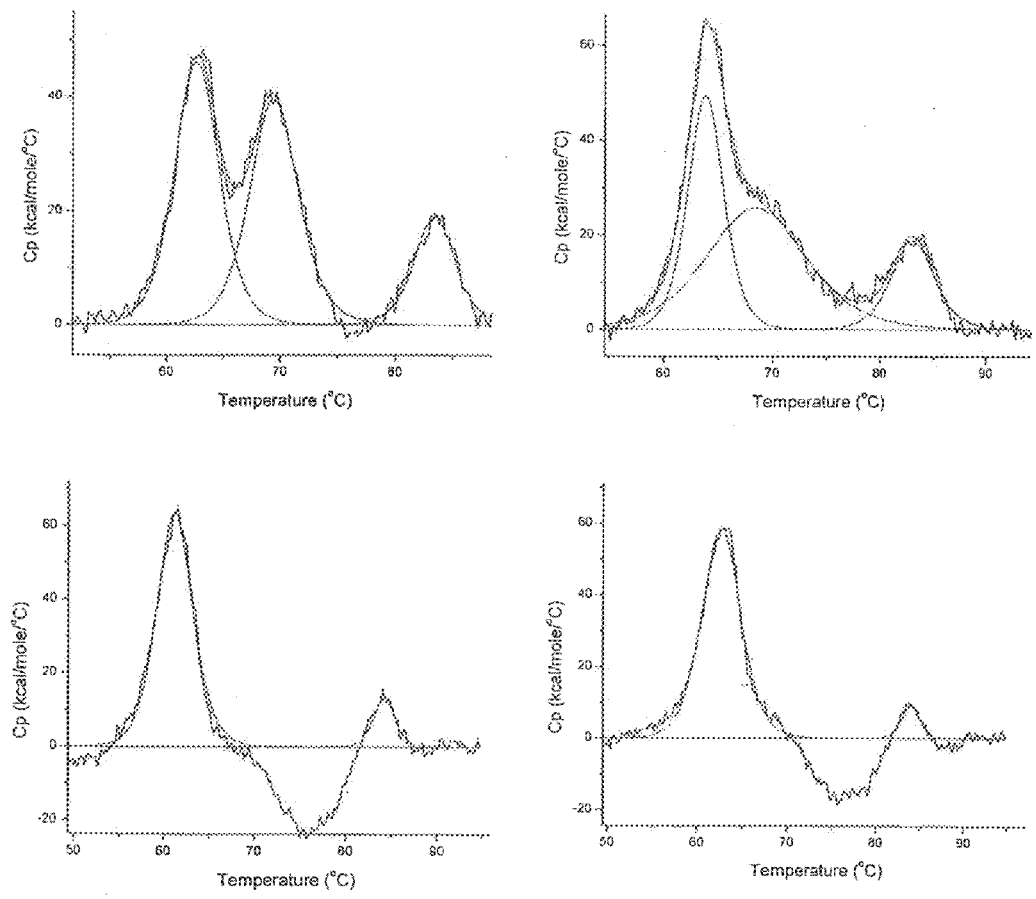
FIG. 8 shows thermal stabilities of chicken and CHO cell derived MAbF1. DSC data of MAbF1 derived from CHO cells (top left) and chicken tubular gland cells (top right). Data is deconvoluted to fit a two-state transition model with three peaks in both cases (shown in red), yielding $T_m$ values of 62.7, 69.4 and 83.4° C. for antibody expressed in CHO cells and $T_m$ values of 63.8, 68.5 and 83.1° C. for the chicken derived antibody. The DSC data of the respective Fc-deglycosylated antibodies (bottom left and bottom right respectively), were also fitted to a two-state transition model, but with 2 peaks in each case, which yields $T_m$ values of 61.2 and 84.0° C. for the CHO expressed antibody and 62.6 and 84.0° C. for the chicken derived antibody.

The unfolding profiles of the CHO and chicken derived antibodies are quite different whereas the unfolding profiles of the Fc-deglycosylated antibodies are almost identical (FIG. 8). These data suggest that glycosylation of MAbF1 produced in chicken tubular gland cells confers greater thermal stability than the carbohydrate residues attached to MAbF1 produced in CHO cells.

5. Oligosaccharide Characterization of MAb by CE-LIF

Figure 9:
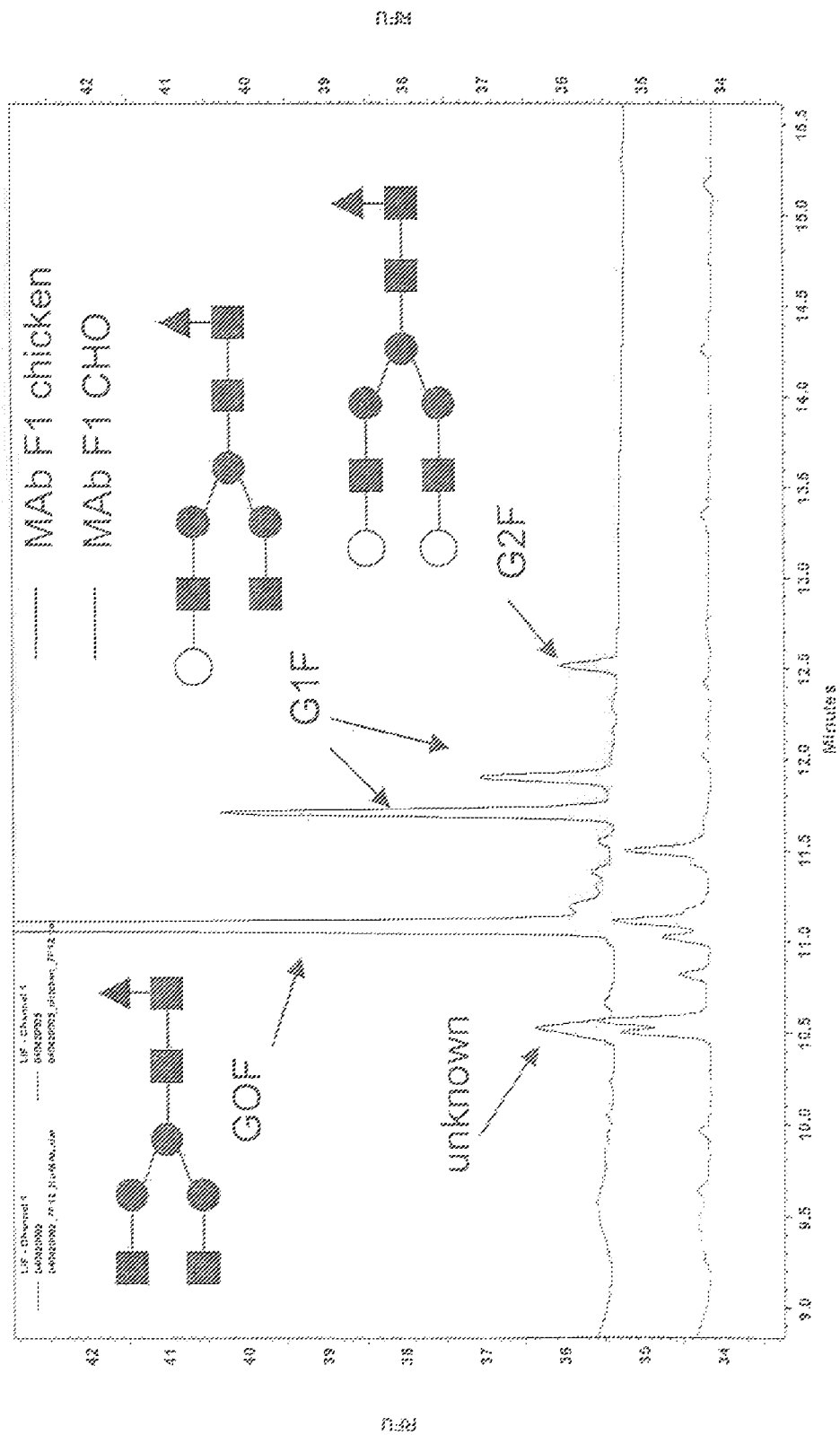
FIG. 9 shows the oligosaccharide profiles of MAbF1 produced in chicken tubular gland cells and in CHO cells. Known glycan structures of the CHO-produced MAb are indicated. Mannose is shown as a black circle; galactose is shown as an open circle; N-acetyl glucosamine is shown as a black square; fucose is shown as a black triangle.

Oligosaccharides were released from IgG samples (100µγ) by overnight incubation of the samples with 12.5 mU PNGaseF (Prozyme) at 40° C. Under the conditions used, the N-linked glycans from the Fc portion of HuMAbF1 expressed in CHO cells and chicken were released. Following ethanol precipitation to remove MAb protein, the supernatant containing the glycans was dried by vacuum centrifugation and resuspended in 19 mM APTS (Beckman) in 15% acetic acid and 1 M sodium cyanoborohydride in THF (Sigma). The glycan labeling reaction was allowed to continue overnight at 40° C. followed by 25-fold dilution of sample in water. APTS-labeled glycans were applied to capillary electrophoresis with laser induced fluorescence on a P/ACE MDQ CE system (Beckman) with reverse polarity, using a 50 µm internal diameter N—CHO coated capillary (Beckman) with 50 cm effective length. Samples were pressure (8 sec.) injected and separation was carried out at 20° C. using Carbohydrate Separation Gel Buffer (Beckman) at 25 kV for 20 min. The separations were monitored using a laser-induced fluorescence detection system (Beckman) with a 3 mW argon ion laser and excitation wavelength of 488 nm and emission of 520 nm. As shown in FIG. 9, the oligosaccharide profile of MAbF1 produced in the chicken was found to be quite different from that of MAbF1 produced in the CHO cells.

6. Oligosaccharide Characterization of MAb by MALDI Q-TOF MS.

Purified antibodies (100 µg each at 1.0 mg/ml) were treated with 4 µl of PNGaseF, an endoglycosidase that cleaves N-linked carbohydrates (Prozyme). The samples were incubated at 37° C. overnight followed by dialysis overnight against 50 mM ammonium bicarbonate (pH 8). The protein was removed by ethanol precipitation. The released carbohydrates were desalted on a micro carbon column from Glygen Corp. (Columbia, Md.) essentially following the vendor's protocol, but the elution volume was reduced to 5 µl. A 1 µl aliquot of each glycan sample was mixed 1:1 (v:v) with matrix solution (α-cyano-4-hydroxycinnamic acid or 2,5-dihydroxybenzoic acid (Applied Biosystems), spotted on a MALDI target plate and allowed to air-dry. MALDI-Q-TOF tandem analysis was used to perform the analysis of intact glycoconjugates. All mass spectra were recorded on a QSTAR pulsar i mass spectrometer equipped with an o-MALDI source 2 (MDS Sciex, Concord, Ontario, Canada), which provides the mass (composition) of classes of carbohydrates. After the glycan profiling of both the MAbs, the possible glycosidic linkage in each glycan was investigated. High CID mass spectra were recorded on a 4700 Proteomics analyzer with a TOF/TOF optics (Applied Biosystems, Forster City, Calif.). For high CID MS/MS experiments, the collision energy was set at 1 kV. Inside the collision cell, the selected oligosaccharide ions were collided with argon at a pressure of $2 \times 10^{-6}$ Torr. The carbohydrate composition and possible glycosidic linkages of eleven major glycans in chicken-derived MAbF1 analyzed by MALDI TOF mass spectrometry are summarized in Table 13. The oligosaccharide structures were found to contain high-mannose type, complex type and hybrid type N-glycans.

Table 13 Carbohydrate analysis of MAbF1 produced in chicken by mass spectrometry (see attachment)

TABLE 13

Carbohydrate analysis of MAbF1 produced in chicken by mass spectrometry

| Observed mass + Na+ | Theoretical mass + Na+ | Composition | Possible structure |
|---|---|---|---|
| 1136.4 | 1136.5 | (Man)$_3$(GlcNAc)$_3$ | 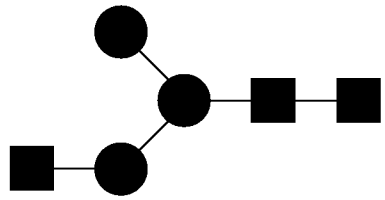 |

TABLE 13-continued
Carbohydrate analysis of MAbF1 produced in chicken by mass spectrometry
| Observed mass + Na+ | Theoretical mass + Na+ | Composition | Possible structure |
|---|---|---|---|
| 1257.4 | 1257.6 | (Hex)$_2$(Man)$_3$(GlcNAc)$_2$ | 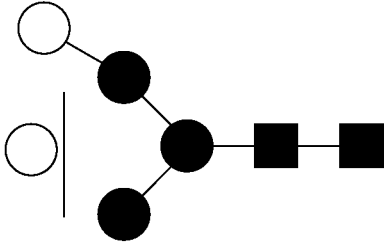 |
| 1298.4 | 1298.44 | (Hex)(Man)$_3$(GlcNAc)$_3$ | 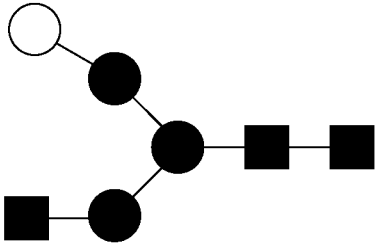 |
| 1339.46 | 1339.5 | (Man)$_3$(GlcNAc)$_4$ | 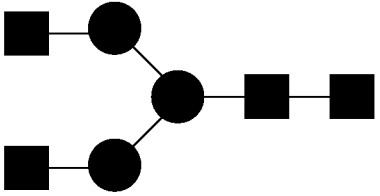 |
| 1460.49 | 1460.5 | (Hex)$_2$(Man)$_3$(GlcNAc)$_3$ | 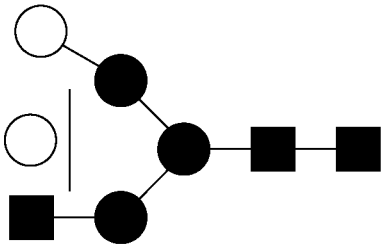 |
| 1501.53 | 1501.5 | (Hex)(Man)$_3$(GlcNAc)$_4$ | 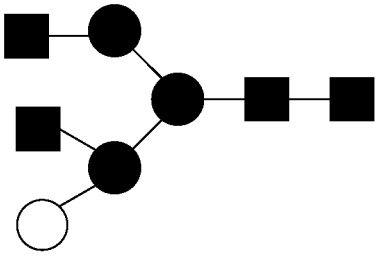 |
| 1542.56 | 1542.6 | (Man)$_3$(GlcNAc)$_5$ | 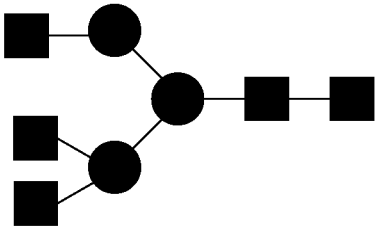 |

TABLE 13-continued

Carbohydrate analysis of MAbF1 produced in chicken by mass spectrometry

| Observed mass + Na+ | Theoretical mass + Na+ | Composition | Possible structure |
|---|---|---|---|
| 1663.6 | 1663.58 | (Hex)$_2$(Man)$_3$(GlcNAc)$_4$ | (structure shown) or (structure shown) |
| 1704.6 | 1704.6 | (Hex)(Man)$_3$(GlcNAc)$_5$ | (structure shown) |
| 1745.66 | 1745.6 | (Man)$_3$(GlcNAc)$_6$ | (structure shown) |
| 1866.7 | 1866.7 | (Hex)$_2$(Man)$_3$(GlcNAc)$_5$ | (structure shown) |
| 1948.7 | 1948.68 | (Man)$_3$(GlcNAc)$_7$ | Not determined |

Man, mannose, shown as black circle; Hex, hexose (mannose or galactose), shown as open circle; GlcNAc, N-acetyl glucosamine, shown as black square. The vertical line indicates that the last hexose could be connected to any one of Man or GlcNAc residues along the line.

7. Monosaccharide Analysis by HPLC with HPAE-DAD.

TABLE 14

Monosaccharide analysis of chicken produced and CHO produced MAbF1

| Monosaccharide | CHO HuMAb pmol (% total) | Chicken HuMAb pmol (% total) |
|---|---|---|
| Fucose | 692 (18) | 0 |
| Glucosamine | 1,536 (40) | 1,571 (52) |
| Galactose | 671 (17) | 43 (1) |
| Mannose | 940 (25) | 1,513 (47) |
| Total | 3,839 (100) | 3,127 (100) |

IgG samples (200 μg) were subjected to acid hydrolysis using either 2 N TFA (for estimating neutral sugars) or 6 N HCl (for estimating amino sugars) at 100° C. for 4 h. Samples were dried by vacuum centrifugation at ambient temperature and were reconstituted in 200 μl water prior to analysis by HPAE-PAD (Dionex). Monosaccharides were separated using a CarboPac PA10 4×250 mm column with pre-column Amino Trap and Borate Trap (Dionex). Procedures were followed according to Dionex Technical Note 53. Monosaccharide peak identity and relative abundance were determined using monosaccharide standards (Dionex). Monosaccharide analysis of chicken and CHO produced MAbF1 as summarized in Table 14 revealed a difference in carbohydrate composition and showed the presence of N-acetyl glucosamine residues, mannose residues, and very low content of galactose residues in MAbF1 produced in chicken.

8. Summary of Chemical Properties.

In summary, the most striking differences in the N-linked oligosaccharide profiles were the presence of high mannose type N-glycans, the absence of fucose and the very low content of galactose residues in the antibody produced in the chicken. These properties are important for several reasons. Firstly, there is no evidence of a α1-3 Gal linkages, which are known to be antigenic. The reduction in galactose concentrations, typically to levels less than approximately 2% substantially reduces antigenicity resulting from the galactose-containing linkages. Secondly, there is no evidence for N-glycolylneuraminic acid residues, which are also known to be antigenic. Thirdly, the antibody produced in chicken tubular gland cells are substantially free of fucosyl residues, which enhances the ADCC activity of antibodies. In this context, substantially free is defined as less than 0.1%. Fourth, the chicken produced antibody has a high mannose content, typically greater than 40%, which increases the rate of clearance of this antibody when clearance was assessed in Balb/c mice using antibody produced in a CHO cell as the standard. Together with these advantageous chemical properties, the antibodies are present in egg white at concentrations not observed with transgenes that are randomly integrated into the chicken genome or which are not expressed in a tissue specific manner. Preferred concentrations are greater than one mg of antibody per egg, greater than 2 mg per egg, greater than 3 mgs per egg, and as high as 6 mgs per egg. Because each egg comprises approximately 25 ml of egg white, preferred concentrations are greater than 40 μg/ml, greater than 80 μg/ml, greater than 120 μg/ml, and as high as 240 μg/ml.

Example 7

Extraction and Purification of Antibody from Egg White

Figure 10:
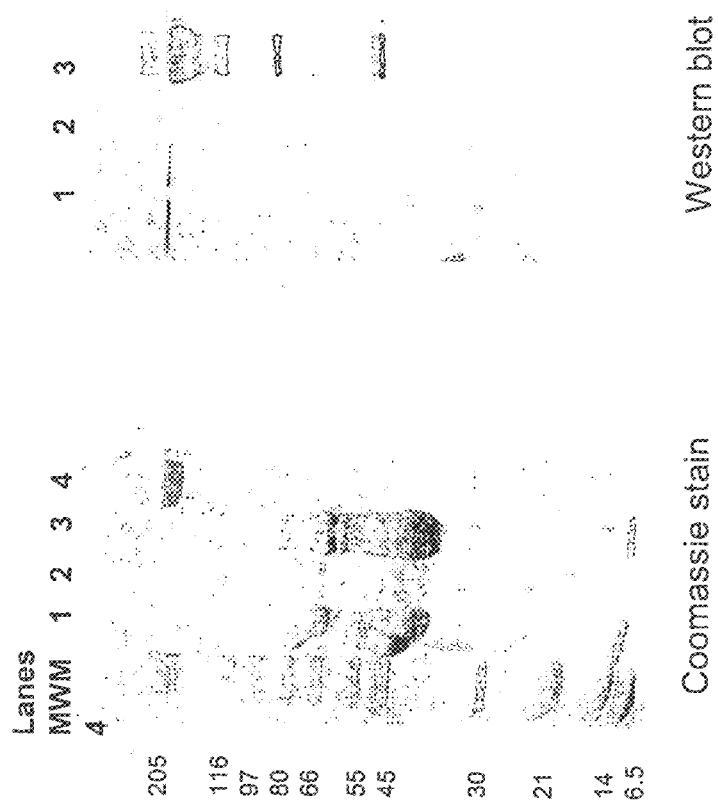
FIG. 10 shows purification of MAbF1 from egg white. 1: Starting material; 2: Protein A load; 3: Protein A flow through; 4: Protein A elute. Both Coomassie stain and Western blot are under non-reducing conditions. HRP-labeled goat anti-human IgG (Southern Biotechnology) was used for detection in the Western blot.

Egg white was first mixed at a low shear rate for 30 min at room temperature and then ovomucin precipitated by a modified method described previously. One volume of homogenized egg white suspension was added to three volumes of reverse osmosis water and stirred for 30 min. The diluted suspension was adjusted to pH 6.0 using 0.5 M phosphoric acid and then centrifuged for 20 min at 12,100 g. Approximately 3% of the egg white protein containing mostly ovomucin was removed by this method. The supernatant was adjusted to pH 7.4 using 0.5 M dibasic sodium phosphate and 150 mM sodium chloride concentration with crystalline salt. The human IgG was purified on a Protein A-Sepharose FF column (Amersham Biosciences) at a 120 cm/h linear flow rate. The adsorbed human IgG was washed with five column volumes of the loading buffer (PBS, pH 7.4) and then eluted with 3 mM phosphoric acid. The eluted human IgG fraction was adjusted to pH 7.5 using 60 mM sodium phosphate (pH 7.5) containing 230 mM NaCl to achieve a final concentration of 40 mM sodium phosphate and 150 mM NaCl. The sample was then filtered through a 0.2 mm syringe filter (Pall). As shown in FIG. 10, most of the purified material was a fully assembled $H_2L_2$ with a purity greater than 90% (determined by ELISA and A280, data not shown).

Example 8

Assay for Binding Affinity

Figure 11:
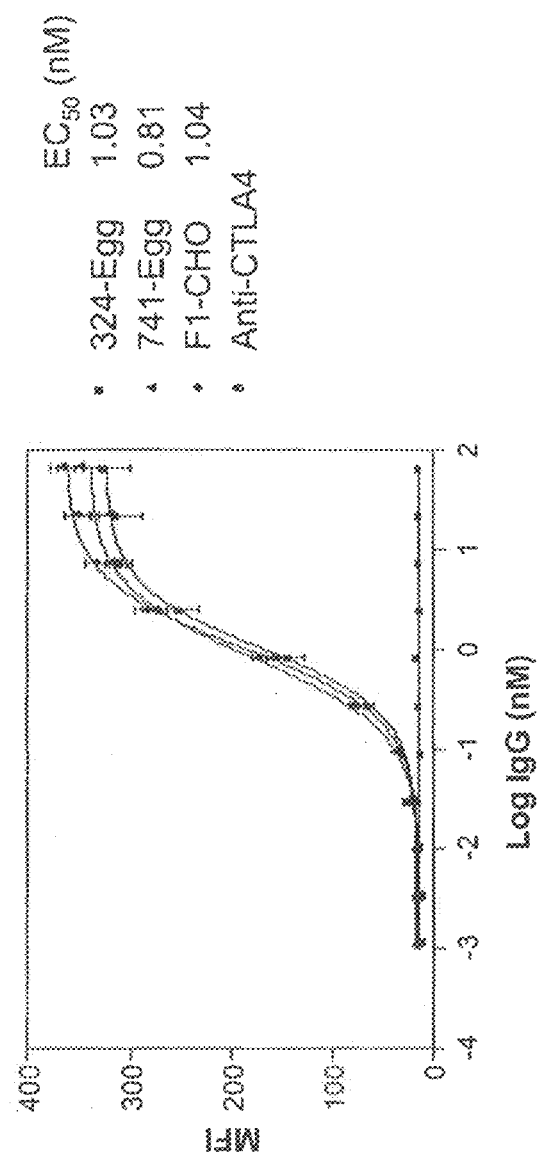
FIG. 11 shows the binding of chicken or CHO cell produced MAbF1 to PSMA expressed on LNCaP cells. 324-Egg and 741-Egg are two different preparations of MAbF1 isolated from eggs. F1-CHO is MAbF1 produced by CHO cells. Anti-CTLA4 is a human IgG1 control MAb not recognizing antigen on LNCaP cells.

PSMA on LNCaP cells (ATCC) was used as antigen to assay for binding. Two hundred thousand cells/well were incubated in duplicate for 30 minutes with 50 μl aliquots of antibody at the indicated concentrations. Cells were washed twice before addition of goat anti-human IgG PE labeled antibody (Jackson ImmunoResearch) at 1:200 dilution, 50 μl/well for 30 minutes at 4° C. Cells were washed twice in PBS with 1% BSA and assayed by FACS. $EC_{50}$ values of MAb binding to PSMA on LNCaP cells were determined from binding curves utilizing GraphPad Prism 3.0 (GraphPad Software). Cells were grown in RPMI 1640 medium supplemented with 10% FBS, 10 mM HEPES, 2 mM L-glutamine, and 1 mM sodium pyruvate. The antigen binding property of MAbF1 produced in chicken tubular gland cells was compared with that of MAbF1 produced in CHO cells. Both antibody preparations produced nearly identical binding curves to PSMA expressed on LNCaP cells with similar $EC_{50}$ values (FIG. 11). The data demonstrate that while the chicken-derived and CHO-derived antibodies are glycosylated differently, they recognize and bind antigen equivalently.

Example 9

Antibody Internalization Assay

Figure 12:
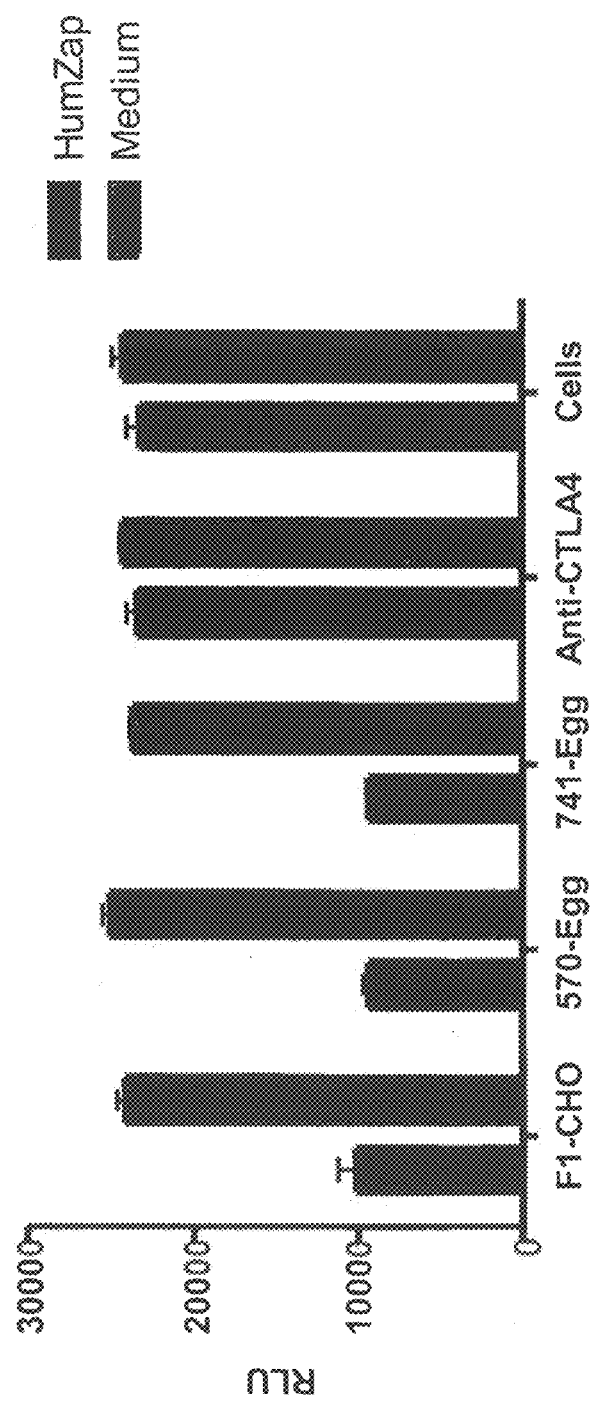
FIG. 12 is the internalization assay of MAbF1 produced in chicken tubular gland cells and CHO cells. 570-Egg and 741-Egg were two preparations of MAbF1 isolated from egg. 300 ng/well each of MAb was added either with Hum-Zap (anti-Human IgG, Saporin conjugate) or cell culture medium to LNCaP Cells. Cell viability was determined 48 hours after addition of MAb and HumZap. The Y axis is Relative Luminescence Units (RLU).

Binding of the MAbF1 to PSMA leads to internalization of the antibody. In one potential application, MAb could be conjugated with cytotoxins in order to target and destroy PSMA-expressing tumor cells. Internalization of antibody binding to PSMA on LNCaP cells was determined by incubating cells, with MAb and Hum-Zap (Advanced Targeting Systems). HumZap is a goat anti-human IgG antibody conjugated to the ribosome inactivating protein, saporin. Cells are killed when the MAbF1/Hum-Zap complex binds to PSMA on the cell surface and is internalized whereas antibody or Hum-Zap alone is not toxic to LNCaP cells. LNCaP cells (10,000/well) were incubated in triplicate, for 48 hours, at 37° C., in 150 μl of culture medium containing 300 ng Hum-Zap, and 300 ng of F1 MAb, or control MAb. Cell proliferation and survival was determined with the CellTiter- Glo Luminescent Cell Viability Assay (Promega). Internalization assays were also done by incubating dilutions of antibody in cell culture medium with 10,000 adherent LNCaP cells/well, for 2 hours at 4° C. Antibody solutions were gently removed and replaced with 150 µl of medium containing 200 ng of HumZap. Cell viability was determined following 48 hours of incubation at 37° C. $EC_{50}$ values for antibody internalization were determined graphically with Prism 3.0 (GraphPad Software). As shown in FIG. 12, both antibody preparations internalized with a similar efficiency. When tested over a range of antibody concentrations, the $EC_{50}$ values for internalization of both the chicken-derived and CHO-derived MAbF1 were 0.49 nM.

Example 10

Clearance of MAb in BALB/c Mice

Figure 13:
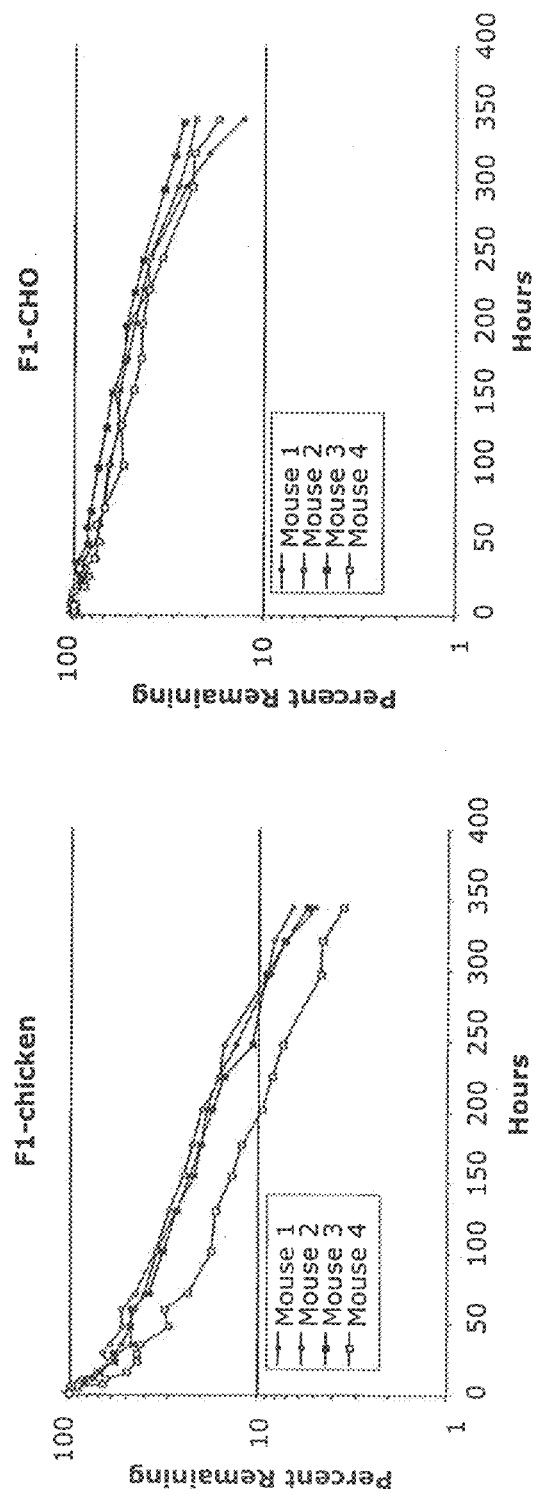
FIG. 13 shows in vivo clearance of MAbF1 produced in chicken tubular gland cells (F1-chicken) and CHO cells (F1-CHO). Four BALB/c mice were injected with each radiolabeled antibody preparation. The residual radioactivity was measured over a period of 350 hours using a whole-body counter. Data are expressed as the percentage of the injected dose remaining.

The in vivo half-life of the chicken produced MAbF1 was analyzed in parallel with the CHO produced antibody in BALB/c mice by intravenous injection of radiolabeled antibodies. Ten µg of MAb protein were lightly iodinated (less than one I per antibody) with $^{125}$I using the Iodobead method (Pierce). Six week-old female BALB/c mice (Taconic Farms, Germantown, N.Y.) were fed 0.1 mg/ml potassium iodide in their drinking water for one week prior to the experiment. Four mice per protein were injected intravenously into the tail vein with approximately 600,000 cpm of labeled MAb and whole body radioactivity was measured at selected times using a whole body gamma counter (Wm. B. Johnson NaI crystal detector with a Ludlum scaler). Half-life was calculated by exponential regression analysis of the residual radioactivity. As shown in FIG. 13, MAbF1 produced by chicken tubular gland cells cleared with a half-life ($t_{1/2}$) of 102.4±0.9 hours, while MAbF1 produced by CHO cells cleared more slowly with a half-life of 207.5±18.3 hours.

Example 11

Assay for ADCC

LNCaP-C42B cells were tested in a modified $^{51}$Cr ADCC assay. Human peripheral blood mononuclear cells were purified from heparinized whole blood by standard Ficoll-paque separation. The cells were resuspended (at 1×10E6 cells/mL) in RPMI1640 media containing 10% FBS and 10 U/ml of human IL-2 and incubated overnight at 37° C. The following day, the cells were collected and washed once in culture media and resuspended at $2 \times 10^7$ cells/ml. Two million target LNCaP-C42b cells are incubated with 200 uCi $^{51}$Cr in 1 ml total volume for 1 hour at 37° C. The target cells are washed once, resuspended in 1 ml of media, and incubated at 37° C. for an additional 30 minutes. After the final incubation, the target cells are washed once and brought to a final volume of $1 \times 10^5$ cells/ml. For the final ADCC assay, 100 µl of labeled LNCaP cells are incubated with 50 µl of effector cells and 50 µl of antibody. The final target to effector ratio of 1:100 was selected. In all studies, human IgG1 isotype control is run and compared to CHO-derived anti-PSMA MAbF1 antibody. Other controls which are included are: a) target and effector cells but no antibody, b) target cells with no effector cells and c) target and effector cells in the presence of 3% Triton X-100. Following 4 hour incubation at 37° C., the supernatants were collected and counted on a gamma Counter (Cobra II auto-gamma from Packard Instruments) with a reading window of 240-400 keV. The counts per minute were plotted as a function of antibody concentration and the data was analyzed by non-linear regression, sigmoidal dose response (variable slope) using Prism software (San Diego, Calif.). The percent lysis was determined by the following equation:

% Lysis=(Sample CPM–No antibody CPM)/TritonX CPM–No antibody CPM)×100

We have found that it is important that both $EC_{50}$ values and % Lysis are monitored in all studies. For example, it is possible when comparing two antibodies to have a change in either the $EC_{50}$ or % lysis or both.

Blockade of ADCC with anti-CD 16 antibodies was conducted with the following modifications. The cells were incubated with either 1 or 0.01 □g/ml of CHO produced or chicken produced MAbF1 antibodies in the absence or presence of 5 □g/ml of anti-CD 16 antibody 3G8 or isotype control antibody.

Figure 14:
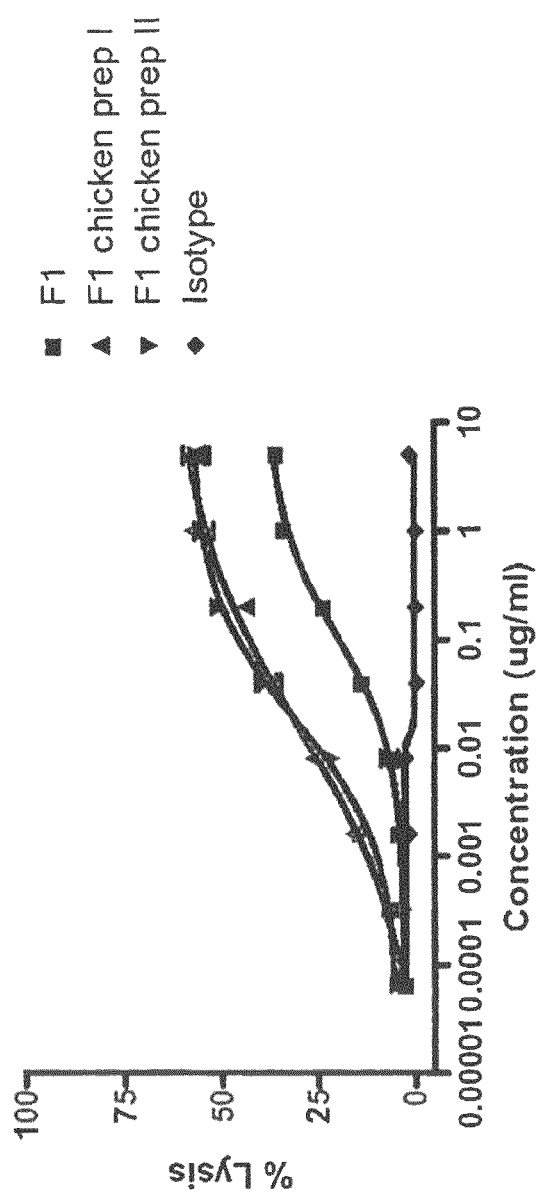
FIG. 14 shows ADCC assay of MAbF1 produced in chicken tubular gland cells (F1 chicken prep I and II) and CHO cells (F1) in the presence of human IL-2. A human IgG1 not recognizing antigen on LNCaP cells was used as isotype control.
Figure 15:
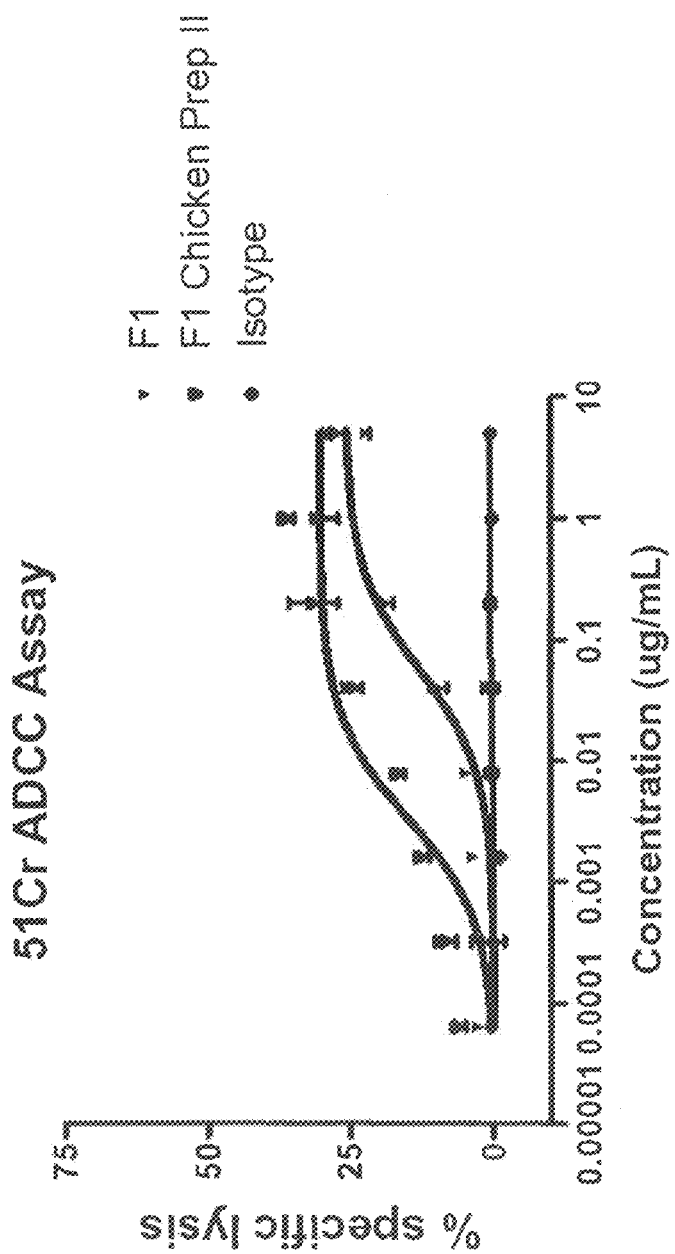
FIG. 15 shows ADCC assay of MAbF1 produced in chicken tubular gland cells (F1 chicken prep I and II) and CHO cells (F1) in the absence of human IL-2. A human IgG1 not recognizing antigen on LNCaP cells was used as isotype control.

FIG. 14 shows that CHO-derived MAb induces dose dependent cell lysis which reaches a plateau at 38% lysis with an $EC_{50}$ of 0.11 µg/ml with IL-2 stimulated effector cells. In contrast, the chicken egg derived MAb was more potent and more efficatious. The maximum % lysis of the chicken egg derived MAb was 60% with two different preparations of the antibody. The enhanced potency over the CHO derived MAb was also demonstrated as the $EC_{50}$ of this material was 0.018 µg/ml. Finally, as expected, isotype control antibody did not induce cell lysis. ADCC with unstimulated effector cells (fresh PBMCs) shows a greater difference in EC50 values, but lower overall cell killing (FIG. 15)

Figure 16:
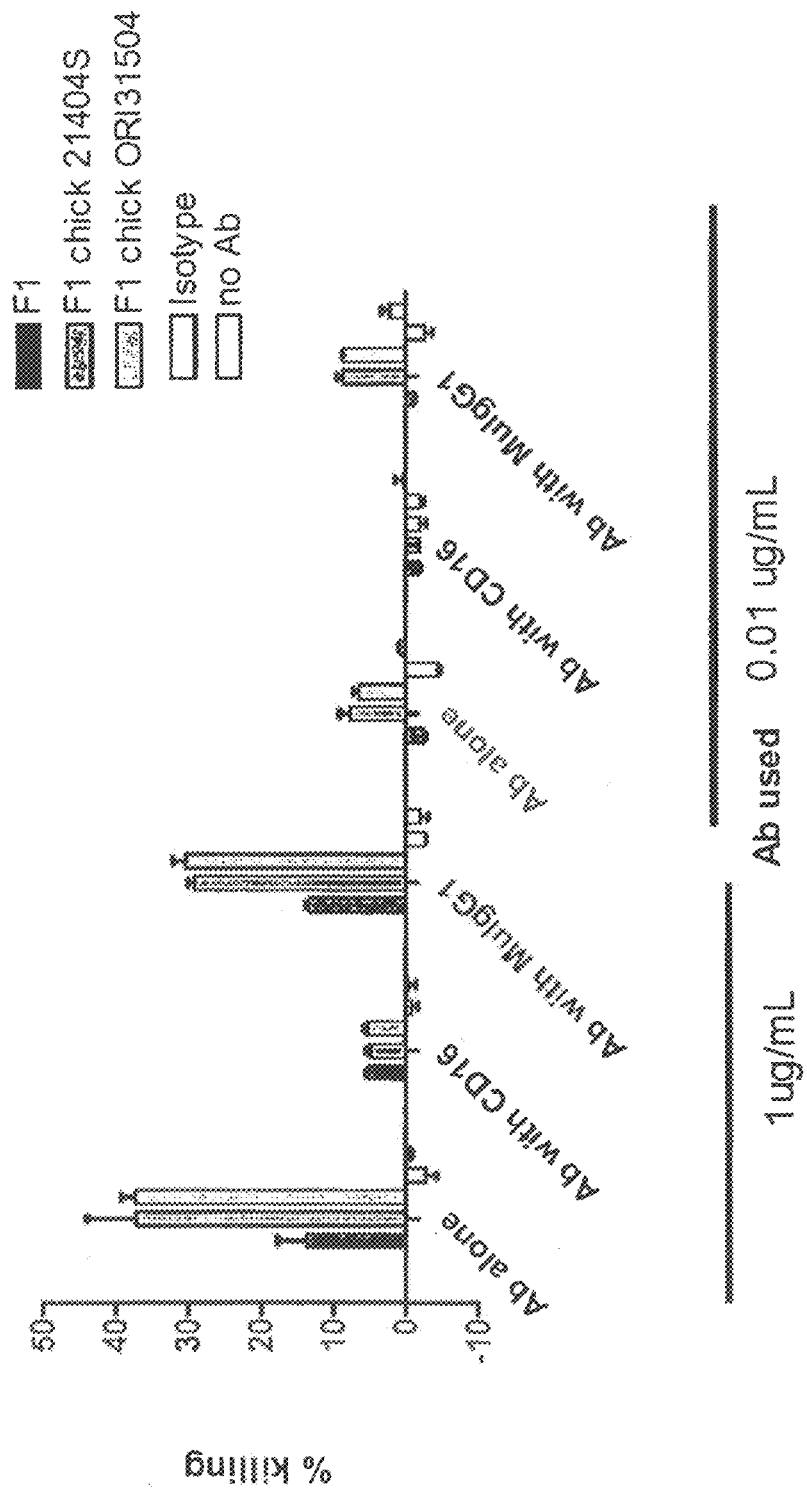
FIG. 16 shows the blockade of ADCC with anti-CD16 antibodies.

CD16 (FCgRIII) is a key receptor that mediates ADCC. The specificity of the ADCC response was shown by blocking the interaction of target and effector cells using a monoclonal antibody directed against CD16. In this study, two doses of MAbF1 antibody were used, a saturating dose (1 µg/ml) and a sub-optimal dose (0.01 µg/ml). One µg/ml of MAbF1 antibody, in the absence of anti-CD16 antibody, induced approximately 15% and 38% lysis with CHO-derived and chicken-derived antibody, respectively. This % lysis was reduced to ~4% in the presence of anti-CD16 antibody while isotype control antibody had no effect (FIG. 16).

Example 12

CD16 Binding

CHO and Chicken derived MAbF1s were immobilized to a carboxymethyl dextran matrix surface of a Biacore sensor chip (CM5) via primary amines, using amine coupling kit provided by Biacore. Both antibodies were coated to a density of about 10,000 RUs. The binding of the two antibodies with CD16-Phe and CD16-Val were carried out by flowing several concentrations of the proteins over the immobilized antibody surfaces. Non-specific binding effects were accounted for by considering blank surfaces and plain buffer binding cycles. FIBS-EP buffer was used for dilutions and as running buffer. The experiment was conducted at 25° C. on a Biacore-3000 instrument. Data was analyzed using GraphPad Prism software and data was fitted to a single binding site model to estimate the equilibrium dissociation constant.

Figure 17:
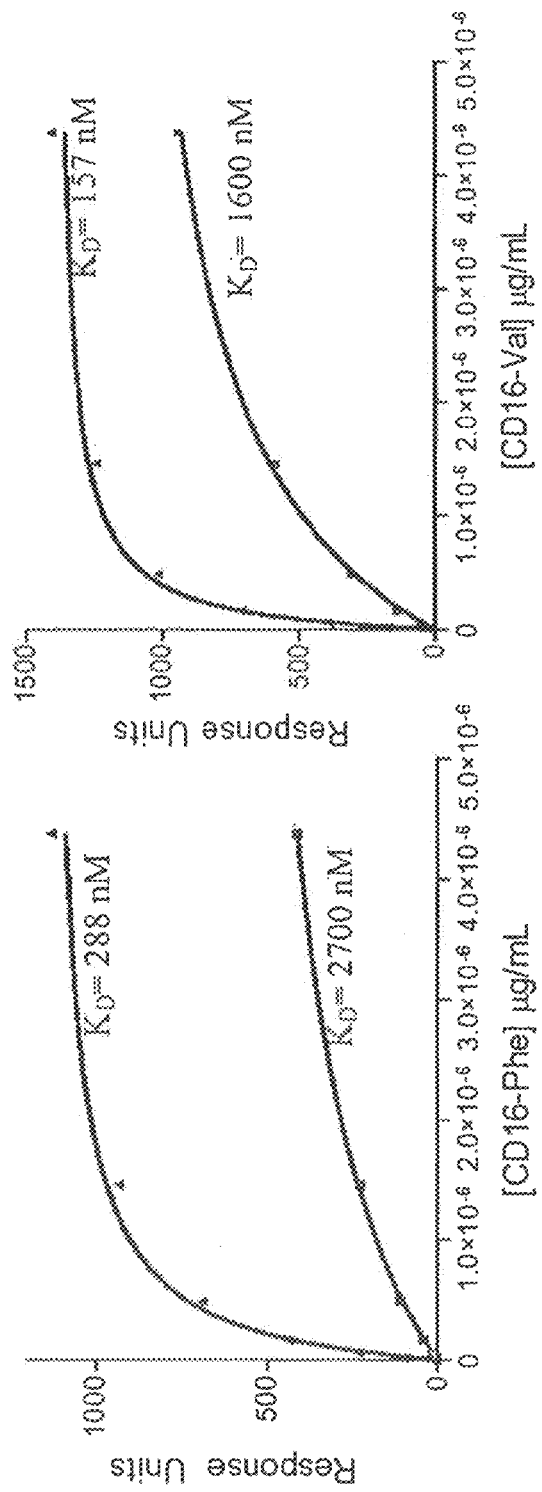
FIG. 17 shows equilibrium binding of Chicken (blue) and CHO (red) derived MAbF1 with CD16-Phe (left panel) and CD16-Val (right panel). Estimated values of dissociation constants ($K_D$) are shown near corresponding fits.

The dissociation constant was estimated based on equilibrium binding experiments rather than rate constants, since fast kinetics is a characteristic feature of FcRs binding to antibodies. The curve fits used for estimation of $K_D$ are shown in FIG. 17. The dissociation constant, $K_D$, of chicken derived antibody is about ten fold lower for both the FcRs, compared to the corresponding CHO derived antibody. The higher affinity of the chicken derived antibody may be attributable to the differences in the glycosylation in the Fc region, especially due to the absence of fucose, which is present in the CHO derived antibody.

Example 13

Therapeutic Utility

The present invention provides antibodies having specifically defined glycosylation patterns and other chemical properties and which have been generated using the genetically modified chicken described above. These properties provide improved therapeutic properties when administered to a patient for the purpose of binding to antigen-specific targets in target tissue. Specifically, as noted above, for certain clinical indications, the antibodies exhibit enhanced antibody-dependent cellular cytotoxicity (ADCC) and this effect offers important advantages in certain clinical indications.

Clinical trials of unconjugated monoclonal antibodies (mAbs) for the treatment of some types of cancer have yielded encouraging results. Dillman, 1997, Cancer Biother. & Radiopharm. 12:223-225; Deo et al., 1997, Immunology Today 18:127. A chimeric, unconjugated IgG1 has been approved for low-grade or follicular B-cell non-Hodgkin's lymphoma (Dillman, 1997, supra), while another unconjugated mAb, a humanized IgG1 targeting solid breast tumors, has also shown promising results in phase III clinical trials. Deo et al., 1997, supra. The antigens of these two MAbs are highly expressed in their respective target tissue. For such applications, particularly in tumor cells where the antibodies mediate potent tumor destruction by ADCC, the antibodies of the present invention offer therapeutic advantages upon administration to a patient.

For therapeutic uses, an antibody of the invention can also be functionally linked (e.g., by chemical coupling, genetic fusion, noncovalent association or otherwise) to one or more other molecular entities, such as another antibody (e.g., to produce a bispecific or a multispecific antibody), a cytotoxin, cellular ligand or antigen (e.g., to produce an immunoconjugate, such as an immunotoxin). An antibody of the present invention can be linked to other therapeutic moieties, e.g., a radioisotope, a small molecule anti-cancer drug, an anti-inflammatory agent, a cytotoxin or an immunosuppressive agent. Accordingly, the present invention encompasses antibody compositions having chemical properties enabled by the chicken expression system and combined with essentially all known antibody conjugation, linking, and related technology for therapeutic use.

Accordingly, antibodies of the present invention can be used to treat and/or prevent a variety of diseases involving cells expressing antigen in a target tissue that is susceptible to treatment, particularly when the ADCC mechanism is exhibited in target tissue. Exemplary diseases that can be treated (e.g., ameliorated) or prevented include, but are not limited to solid tumors, lymphomas, diffuse tumors, and cancerous tissues of all types.

In a therapeutic embodiment of the invention, a patient is administered the antibody of the invention specifically in accord with a diagnosis of a condition that would be treated by a modality exhibiting the property of ADCC. In such a clinical setting, the antibodies of the invention are administered and the cellular cytotoxic effect of the treatment is determined following the treatment to determine the ADCC effect in target tissue. In addition to the therapeutic compositions of the invention, the patient may be additionally treated with a chemotherapeutic agent, radiation, or an agent that modulates, e.g., enhances or inhibits, the expression or activity of an Fc receptor, such as a cytokine. Typical, cytokines for administration during treatment include granulocyte colony-stimulating factor (G-CSF), granulocyte-macrophage colony-stimulating factor (GM-CSF), interferon-γ (IFN-'γ), and tumor necrosis factor (TNF). Typical therapeutic agents include, among others, anti-neoplastic agents such as doxorubicin, cisplatin, bleomycin, carmustine, chlorambucil, and cyclophosphamide.

In another aspect, the present invention provides a composition, e.g., a pharmaceutical composition, containing one or a combination of the chicken-expressed antibodies of the present invention. A composition of the present invention can be administered by a variety of methods known in the art. As will be appreciated by the skilled artisan, the route and/or mode of administration will vary depending upon the desired results. Pharmaceutically acceptable carriers include sterile aqueous solutions or dispersions and the use of such media and agents for pharmaceutically active substances is known in the art. Sterile injectable solutions can be prepared by incorporating the active compound in the required amount in an appropriate solvent with one or a combination of ingredients followed by sterilization and/or microfiltration. Generally, dispersions are prepared by incorporating the active compound into a sterile vehicle that contains a basic dispersion medium and any other ingredients.

Dosage regimens are adjusted to provide the optimum desired ADCC effect. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Because the effect of the administration of antibodies of the invention is objectively observable in target tissue such as tumors, the therapeutic methods of the invention include diagnosing a patient in need of therapy, including specifically a therapy using ADCC, identifying target tissue in which the effect is desired, administering the compositions of the invention to the patient in need thereof, and measuring the therapeutic effect in the patient, such as by determining the efficacy of the ADCC in the target tissue of the patient. The determination of therapeutic effect may be achieved by analyzing changes in the properties of the target tissue over time, such as cell death, shrinkage of target tissue, reductions in tumor size, and any other diagnostic technique known in the medical arts.

The antibodies of the invention can also be tested for ADCC activity in any of a number of known models for ADCC available to those skilled in the art. For purposes of determining the utility of the present antibodies for therapeutic or diagnostic use, the measurement of ADCC may be performed independently or compared with other mammalian, non-mammalian, plant, or bacterial cell expression systems. Accordingly, the methods of the invention include determining the difference in utility for purposes of effecting ADCC by using an antibody of the present invention in direct or indirect comparison to another antibody produced in the aforementioned systems. Specifically, this methodology includes comparing the ADCC effect of antibodies produced in the chicken expression system described above to identify enhanced ADCC to identify ideal antibody candidates for the chicken expression system. As noted above, to enhance the therapeutic utility, the antibodies of the invention can be co-administered with one or other more therapeutic agents, e.g., a cytotoxic agent, a radiotoxic agent or an immunosuppressive agent. The antibody can be linked to the agent (as an immunocomplex) or can be administered separate from the agent. In the latter case (separate administration), the antibody can be administered before, after or concurrently with the agent or can be co-administered with other known therapies, e.g., an anti-cancer therapy, e.g., radiation. Such therapeutic agents include, among others, anti-neoplastic agents such as doxorubicin, cisplatin, bleomycin, carmustine, chlorambucil, and cyclophosphamide. Co-administration of the antibodies of the present invention with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells which would render them unreactive with the antibody.

There will be various modifications, improvements, and applications of the disclosed invention that will be apparent to those of skill in the art, and the present application encompasses such embodiments to the extent allowed by law. Although the present invention has been described in the context of certain preferred embodiments, the full scope of the invention is not so limited, but is in accord with the scope of the following claims. All references, patents, or other publications are specifically incorporated by reference herein.

The invention claimed is:

1. A method for producing a human monoclonal antibody substantially free of fucosyl residues comprising:

expressing the antibody in tubular gland cells of a female genetically modified chicken, wherein the genome of the tubular gland cells of said chicken stably comprise and selectively express an exogenous polynucleotide encoding the monoclonal antibody, wherein the exogenous polynucleotide is operably linked to a regulatory sequence of a gene encoding ovalbumin in its 5' and 3' ends, and, wherein the 5' regulatory sequence comprises at least 15 kb of the ovalbumin promoter regulatory sequence and the 3' regulatory sequence comprises at least 15 kb of the 3' regulatory sequence of the ovalbumin gene; and collecting the antibody from eggs laid by the chicken, wherein the antibody is present in the egg white of the eggs laid by the chicken at a concentration of at least 40 µg/ml.

2. The method of claim 1 wherein the antibodies have a mannose concentration of greater than approximately 40%.

3. The method of claim 1 wherein the galactose concentration is less than approximately 2%.

4. A genetically modified female chicken selectively expressing a human monoclonal antibody in tubular gland cells, wherein the monoclonal antibody is encoded by an exogenous polynucleotide stably integrated into the genome of the tubular gland cells, wherein the tubular gland cells are derived from a donor chicken embryonic stem cell, wherein the exogenous polynucleotide is operably linked to a regulatory sequence of a gene encoding ovalbumin in its 5' and 3' ends, wherein the 5' regulatory sequence comprises at least 15 kb of the ovalbumin promoter regulatory sequence and the 3' regulatory sequence comprises at least 15 kb of the 3' regulatory sequence of the ovalbumin gene, and wherein the egg white of an egg laid by said chicken comprises the monoclonal antibody at a concentration of at least 40 µg/ml.

5. The chicken of claim 4 wherein the antibodies are substantially free of fucosyl residues.

6. The chicken of claim 4 wherein the mannose concentration is greater than approximately 40%.

7. The chicken of claim 4 wherein the galactose concentration is less than approximately 2%.

8. The method of claim 1, wherein the antibody has a glucosamine concentration of greater than 50%.

9. The method of claim 1, wherein the antibody is a fully human antibody.

10. The method of claim 1, further comprising linking the fully human monoclonal antibody to an entity selected from the group consisting of another antibody, a cytotoxin, a cellular ligand, a cellular antigen, a radioisotope, a small molecule anti-cancer drug, an anti-inflammatory agent, a cytotoxin and an immunosuppressive agent.

11. The method of claim 1, wherein the exogenous polynucleotide comprises an internal ribosome entry site (IRES).

12. The method of claim 1, wherein a selectable marker is operably linked to the 3' regulatory sequence of the ovalbumin gene.

13. The chicken of claim 4, wherein the antibodies have a glucosamine concentration of greater than 50%.

14. The chicken of claim 4, wherein the antibody is a fully human antibody.

15. The chicken of claim 4, wherein the fully human monoclonal antibody is linked to an entity selected from the group consisting of another antibody, a cytotoxin, a cellular ligand, a cellular antigen, a radioisotope, a small molecule anti-cancer drug, an anti-inflammatory agent, a cytotoxin and an immunosuppressive agent.

16. The chicken of claim 15, wherein the exogenous polynucleotide comprises an internal ribosome entry site (IRES).

17. The chicken of claim 4, wherein a selectable marker is operably linked to the 3' regulatory sequence of the ovalbumin gene.

18. An egg laid by the genetically modified chicken of claim 4.

* * * * *

SEQUENCE LISTING

```
<160> NUMBER OF SEQ ID NOS: 41

<210> SEQ ID NO 1
<211> LENGTH: 13
<212> TYPE: PRT
<213> ORGANISM: Artificial Sequence
<220> FEATURE:
<223> OTHER INFORMATION: Synthesized

<400> SEQUENCE: 1

Ala Val Gln Leu Val Gln Ser Leu Gly Ala Glu Val Lys
 1               5                  10

<210> SEQ ID NO 2
<211> LENGTH: 20
<212> TYPE: PRT
<213> ORGANISM: Artificial Sequence
<220> FEATURE:
<223> OTHER INFORMATION: Synthesized

<400> SEQUENCE: 2

Ala Val Gln Leu Val Gln Ser Leu Gly Ala Glu Val Lys Lys Pro Gly
 1               5                  10                  15

Glu Ser Leu Lys
            20

<210> SEQ ID NO 3
<211> LENGTH: 15
<212> TYPE: PRT
<213> ORGANISM: Artificial Sequence
<220> FEATURE:
<223> OTHER INFORMATION: Synthesized

<400> SEQUENCE: 3

Gly Ser Gly Tyr Ser Phe Thr Ser Phe Trp Ile Gly Trp Ala Arg
 1               5                  10                  15

<210> SEQ ID NO 4
```

```
<211> LENGTH: 20
<212> TYPE: PRT
<213> ORGANISM: Artificial Sequence
<220> FEATURE:
<223> OTHER INFORMATION: Synthesized

<400> SEQUENCE: 4

Gly Ser Gly Tyr Ser Phe Thr Ser Phe Trp Ile Gly Trp Ala Arg Gln
1               5                   10                  15

Met Pro Gly Lys
            20

<210> SEQ ID NO 5
<211> LENGTH: 19
<212> TYPE: PRT
<213> ORGANISM: Artificial Sequence
<220> FEATURE:
<223> OTHER INFORMATION: Synthesized

<400> SEQUENCE: 5

Pro Gly Lys Gly Leu Glu Trp Met Gly Ile Ile Tyr Pro Gly Asp Ser
1               5                   10                  15

Asp Thr Arg

<210> SEQ ID NO 6
<211> LENGTH: 15
<212> TYPE: PRT
<213> ORGANISM: Artificial Sequence
<220> FEATURE:
<223> OTHER INFORMATION: Synthesized

<400> SEQUENCE: 6

Tyr Ser Pro Ser Phe Gln Gly Gln Val Thr Ile Ser Ala Asp Lys
1               5                   10                  15

<210> SEQ ID NO 7
<211> LENGTH: 14
<212> TYPE: PRT
<213> ORGANISM: Artificial Sequence
<220> FEATURE:
<223> OTHER INFORMATION: Synthesized

<400> SEQUENCE: 7

Ser Ile Ser Thr Ala Tyr Leu Gln Val Val Ser Ser Leu Lys
1               5                   10

<210> SEQ ID NO 8
<211> LENGTH: 12
<212> TYPE: PRT
<213> ORGANISM: Artificial Sequence
<220> FEATURE:
<223> OTHER INFORMATION: Synthesized

<400> SEQUENCE: 8

Gly Thr Leu Val Thr Val Ser Ser Ala Ser Thr Lys
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthesized

<400> SEQUENCE: 9

Gly Pro Ser Val Phe Pro Leu Ala Pro Ser Ser Lys
```

```
                1               5                  10

<210> SEQ ID NO 10
<211> LENGTH: 14
<212> TYPE: PRT
<213> ORGANISM: Artificial Sequence
<220> FEATURE:
<223> OTHER INFORMATION: Synthesized

<400> SEQUENCE: 10

Ser Thr Ser Gly Gly Thr Ala Ala Leu Gly Cys Leu Val Lys
  1               5                  10

<210> SEQ ID NO 11
<211> LENGTH: 9
<212> TYPE: PRT
<213> ORGANISM: Artificial Sequence
<220> FEATURE:
<223> OTHER INFORMATION: Synthesized

<400> SEQUENCE: 11

Arg Val Glu Pro Lys Ser Cys Asp Lys
  1               5

<210> SEQ ID NO 12
<211> LENGTH: 4
<212> TYPE: PRT
<213> ORGANISM: Artificial Sequence
<220> FEATURE:
<223> OTHER INFORMATION: Synthesized

<400> SEQUENCE: 12

Val Glu Pro Lys
  1

<210> SEQ ID NO 13
<211> LENGTH: 4
<212> TYPE: PRT
<213> ORGANISM: Artificial Sequence
<220> FEATURE:
<223> OTHER INFORMATION: Synthesized

<400> SEQUENCE: 13

Ser Cys Asp Lys
  1

<210> SEQ ID NO 14
<211> LENGTH: 7
<212> TYPE: PRT
<213> ORGANISM: Artificial Sequence
<220> FEATURE:
<223> OTHER INFORMATION: Synthesized

<400> SEQUENCE: 14

Asp Thr Leu Met Ile Ser Arg
  1               5

<210> SEQ ID NO 15
<211> LENGTH: 7
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (4)...(4)
<223> OTHER INFORMATION: Oxidation
```

```
<400> SEQUENCE: 15

Asp Thr Leu Met Ile Ser Arg
1               5

<210> SEQ ID NO 16
<211> LENGTH: 19
<212> TYPE: PRT
<213> ORGANISM: Artificial Sequence
<220> FEATURE:
<223> OTHER INFORMATION: Synthesized

<400> SEQUENCE: 16

Thr Pro Glu Val Thr Cys Val Val Val Asp Val Ser His Glu Asp Pro
1               5                   10                  15

Glu Val Lys

<210> SEQ ID NO 17
<211> LENGTH: 14
<212> TYPE: PRT
<213> ORGANISM: Artificial Sequence
<220> FEATURE:
<223> OTHER INFORMATION: Synthesized

<400> SEQUENCE: 17

Phe Asn Trp Tyr Val Asp Gly Val Glu Val His Asn Ala Lys
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Synthesized

<400> SEQUENCE: 18

Thr Lys Pro Arg Glu Glu Gln Tyr Asn Ser Thr Tyr Arg
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Synthesized

<400> SEQUENCE: 19

Val Val Ser Val Leu Thr Val Leu His Gln Asp Trp Leu Asn Gly Lys
1               5                   10                  15

<210> SEQ ID NO 20
<211> LENGTH: 12
<212> TYPE: PRT
<213> ORGANISM: Artificial Sequence
<220> FEATURE:
<223> OTHER INFORMATION: Synthesized

<400> SEQUENCE: 20

Val Ser Asn Lys Ala Leu Pro Ala Pro Ile Glu Lys
1               5                   10

<210> SEQ ID NO 21
<211> LENGTH: 8
<212> TYPE: PRT
<213> ORGANISM: Artificial Sequence
<220> FEATURE:
<223> OTHER INFORMATION: Synthesized
```

```
<400> SEQUENCE: 21

Ala Leu Pro Ala Pro Ile Glu Lys
1               5

<210> SEQ ID NO 22
<211> LENGTH: 10
<212> TYPE: PRT
<213> ORGANISM: Artificial Sequence
<220> FEATURE:
<223> OTHER INFORMATION: Synthesized

<400> SEQUENCE: 22

Thr Ile Ser Lys Ala Lys Gly Gln Pro Arg
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthesized

<400> SEQUENCE: 23

Glu Pro Gln Val Tyr Thr Leu Pro Pro Ser Arg
1               5                   10

<210> SEQ ID NO 24
<211> LENGTH: 16
<212> TYPE: PRT
<213> ORGANISM: Artificial Sequence
<220> FEATURE:
<223> OTHER INFORMATION: Synthesized

<400> SEQUENCE: 24

Glu Pro Gln Val Tyr Thr Leu Pro Pro Ser Arg Asp Glu Leu Thr Lys
1               5                   10                  15

<210> SEQ ID NO 25
<211> LENGTH: 10
<212> TYPE: PRT
<213> ORGANISM: Artificial Sequence
<220> FEATURE:
<223> OTHER INFORMATION: Synthesized

<400> SEQUENCE: 25

Asn Gln Val Ser Leu Thr Cys Leu Val Lys
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: (7)...(7)
<223> OTHER INFORMATION: Carbamidomethylation

<400> SEQUENCE: 26

Asn Gln Val Ser Leu Thr Cys Leu Val Lys
1               5                   10

<210> SEQ ID NO 27
<211> LENGTH: 22
<212> TYPE: PRT
```

```
<213> ORGANISM: Artificial Sequence
<220> FEATURE:
<223> OTHER INFORMATION: Synthesized

<400> SEQUENCE: 27

Gly Phe Tyr Pro Ser Asp Ile Ala Val Glu Trp Glu Ser Asn Gly Gln
 1               5                  10                  15

Pro Glu Asn Asn Tyr Lys
            20

<210> SEQ ID NO 28
<211> LENGTH: 22
<212> TYPE: PRT
<213> ORGANISM: Artificial Sequence
<220> FEATURE:
<223> OTHER INFORMATION: Synthesized

<400> SEQUENCE: 28

Thr Thr Pro Pro Val Leu Asp Ser Asp Gly Ser Phe Phe Leu Tyr Ser
 1               5                  10                  15

Lys Leu Thr Val Asp Lys
            20

<210> SEQ ID NO 29
<211> LENGTH: 5
<212> TYPE: PRT
<213> ORGANISM: Artificial Sequence
<220> FEATURE:
<223> OTHER INFORMATION: Synthesized

<400> SEQUENCE: 29

Leu Thr Val Asp Lys
 1               5

<210> SEQ ID NO 30
<211> LENGTH: 18
<212> TYPE: PRT
<213> ORGANISM: Artificial Sequence
<220> FEATURE:
<223> OTHER INFORMATION: Synthesized

<400> SEQUENCE: 30

Glu Ile Val Leu Thr Gln Ser Pro Ala Thr Leu Ser Leu Ser Pro Gly
 1               5                  10                  15

Glu Arg

<210> SEQ ID NO 31
<211> LENGTH: 21
<212> TYPE: PRT
<213> ORGANISM: Artificial Sequence
<220> FEATURE:
<223> OTHER INFORMATION: Synthesized

<400> SEQUENCE: 31

Ala Ser Gln Ser Val Ser Ser Tyr Leu Ala Trp Tyr Gln Gln Lys Pro
 1               5                  10                  15

Gly Gln Ala Pro Arg
            20

<210> SEQ ID NO 32
<211> LENGTH: 9
<212> TYPE: PRT
<213> ORGANISM: Artificial Sequence
<220> FEATURE:
<223> OTHER INFORMATION: Synthesized
```

```
<400> SEQUENCE: 32

Leu Leu Ile Tyr Asp Ala Ser Asn Arg
 1               5

<210> SEQ ID NO 33
<211> LENGTH: 16
<212> TYPE: PRT
<213> ORGANISM: Artificial Sequence
<220> FEATURE:
<223> OTHER INFORMATION: Synthesized

<400> SEQUENCE: 33

Leu Leu Ile Tyr Asp Ala Ser Asn Arg Ala Thr Gly Ile Pro Ala Arg
 1               5                  10                  15

<210> SEQ ID NO 34
<211> LENGTH: 13
<212> TYPE: PRT
<213> ORGANISM: Artificial Sequence
<220> FEATURE:
<223> OTHER INFORMATION: Synthesized

<400> SEQUENCE: 34

Ser Asn Trp Leu Met Tyr Thr Phe Gly Gln Gly Thr Lys
 1               5                  10

<210> SEQ ID NO 35
<211> LENGTH: 23
<212> TYPE: PRT
<213> ORGANISM: Artificial Sequence
<220> FEATURE:
<223> OTHER INFORMATION: Synthesized

<400> SEQUENCE: 35

Leu Glu Ile Lys Arg Thr Val Ala Ala Pro Ser Val Phe Ile Phe Pro
 1               5                  10                  15

Pro Ser Asp Glu Gln Leu Lys
             20

<210> SEQ ID NO 36
<211> LENGTH: 19
<212> TYPE: PRT
<213> ORGANISM: Artificial Sequence
<220> FEATURE:
<223> OTHER INFORMATION: Synthesized

<400> SEQUENCE: 36

Arg Thr Val Ala Ala Pro Ser Val Phe Ile Phe Pro Pro Ser Asp Glu
 1               5                  10                  15

Gln Leu Lys

<210> SEQ ID NO 37
<211> LENGTH: 18
<212> TYPE: PRT
<213> ORGANISM: Artificial Sequence
<220> FEATURE:
<223> OTHER INFORMATION: Synthesized

<400> SEQUENCE: 37

Thr Val Ala Ala Pro Ser Val Phe Ile Phe Pro Pro Ser Asp Glu Gln
 1               5                  10                  15

Leu Lys
```

```
<210> SEQ ID NO 38
<211> LENGTH: 16
<212> TYPE: PRT
<213> ORGANISM: Artificial Sequence
<220> FEATURE:
<223> OTHER INFORMATION: Synthesized

<400> SEQUENCE: 38

Ser Gly Thr Ala Ser Val Val Cys Leu Leu Asn Asn Phe Tyr Pro Arg
1               5                   10                  15

<210> SEQ ID NO 39
<211> LENGTH: 20
<212> TYPE: PRT
<213> ORGANISM: Artificial Sequence
<220> FEATURE:
<223> OTHER INFORMATION: Synthesized

<400> SEQUENCE: 39

Val Asp Asn Ala Leu Gln Ser Gly Asn Ser Gln Glu Ser Val Thr Glu
1               5                   10                  15

Gln Asp Ser Lys
            20

<210> SEQ ID NO 40
<211> LENGTH: 16
<212> TYPE: PRT
<213> ORGANISM: Artificial Sequence
<220> FEATURE:
<223> OTHER INFORMATION: Synthesized

<400> SEQUENCE: 40

Asp Ser Thr Tyr Ser Leu Ser Ser Thr Leu Thr Leu Ser Lys
1               5                   10                  15

<210> SEQ ID NO 41
<211> LENGTH: 24
<212> TYPE: PRT
<213> ORGANISM: Artificial Sequence
<220> FEATURE:
<223> OTHER INFORMATION: Synthesized

<400> SEQUENCE: 41

Val Tyr Ala Cys Glu Val Thr His Gln Gly Leu Ser Ser Pro Val Thr
1               5                   10                  15

Lys Ser Phe Asn Arg Gly Glu Cys
            20
```